United States Patent
Lapen et al.

(10) Patent No.: US 8,454,908 B2
(45) Date of Patent: Jun. 4, 2013

(54) AUTOMATED SYSTEMS AND METHODS FOR PREPARING BIOLOGICAL SPECIMENS FOR EXAMINATION

(75) Inventors: Daniel Lapen, Lancaster, MA (US); David Zahniser, Wellesley, MA (US); Mark Licari, Acton, MA (US); Brian J. McKeen, Bow, NH (US); Eric D. Yeaton, Epsom, NH (US); Dennis Poole, East Derry, NH (US)

(73) Assignee: Constitution Medical, Inc., Boston, MA (US)

( * ) Notice: Subject to any disclaimer, the term of this patent is extended or adjusted under 35 U.S.C. 154(b) by 0 days.

(21) Appl. No.: 13/293,050

(22) Filed: Nov. 9, 2011

(65) Prior Publication Data

US 2012/0149050 A1    Jun. 14, 2012

Related U.S. Application Data

(60) Provisional application No. 61/460,775, filed on Nov. 10, 2010, provisional application No. 61/510,180, filed on Jul. 21, 2011.

(51) Int. Cl.
*A61B 10/00* (2006.01)

(52) U.S. Cl.
USPC ............ 422/536; 422/63; 422/68.1; 422/547; 422/500; 422/501; 422/502; 422/503

(58) Field of Classification Search
USPC ................... 422/63, 68.1, 536, 547, 500–503
See application file for complete search history.

(56) References Cited

U.S. PATENT DOCUMENTS

| | | | |
|---|---|---|---|
| 5,419,279 | A | 5/1995 | Carrico et al. |
| 5,948,360 | A | 9/1999 | Rao et al. |
| 6,096,271 | A | 8/2000 | Loeffler |
| 7,318,913 | B2 | 1/2008 | Loeffler |
| 7,476,543 | B2 | 1/2009 | Becker et al. |
| 7,501,283 | B2 | 3/2009 | Hersch et al. |
| 7,615,371 | B2 | 11/2009 | Kram |
| 7,635,453 | B2 | 12/2009 | Becker et al. |
| 7,744,817 | B2 | 6/2010 | Bui |
| 7,767,152 | B2 | 8/2010 | Stead et al. |
| 7,820,381 | B2 | 10/2010 | Lemme et al. |

(Continued)

FOREIGN PATENT DOCUMENTS

| | | |
|---|---|---|
| EP | 1596972 | 11/2005 |
| EP | 1596974 | 11/2005 |

(Continued)

OTHER PUBLICATIONS

International Search Report and Written Opinion for PCT application No. PCT/US2011/060028, dated Jan. 20, 2012, by Loredana Cipolla.

*Primary Examiner* — Jyoti Nagpaul
(74) *Attorney, Agent, or Firm* — Fish & Richardson P.C.

(57) ABSTRACT

The systems and methods disclosed herein permit automated preparation of biological specimens for examination. The disclosed systems and methods provide fast, efficient, and highly uniform specimen processing using minimal quantities of fluids. The methods include at least a fixing phase for fixing a biological specimen to a substrate such as a microscope slide, a staining phase for staining the specimen, and a rinsing phase for rinsing the specimen. One or more of the fixing, staining, and rinsing phases include one or more agitation cycles for distributing reagents evenly and uniformly across the specimen. The systems can be implemented as a standalone device or as a component in a larger system for preparing and examining biological specimens.

31 Claims, 24 Drawing Sheets

U.S. PATENT DOCUMENTS

| | | |
|---|---|---|
| 8,034,610 B2 | 10/2011 | Erickson et al. |
| 8,038,337 B2 | 10/2011 | Rathgeher et al. |
| 8,058,010 B2 | 11/2011 | Erickson et al. |
| 8,178,350 B2 | 5/2012 | Erickson et al. |
| 2006/0073074 A1 | 4/2006 | Winther |
| 2006/0173575 A1 | 8/2006 | Lefebvre et al. |
| 2006/0239858 A1 | 10/2006 | Becker |
| 2006/0275883 A1 | 12/2006 | Rathgeber et al. |
| 2007/0264161 A1 | 11/2007 | Rathgeber |
| 2008/0102006 A1 | 5/2008 | Kram et al. |
| 2008/0194034 A1 | 8/2008 | Erickson et al. |
| 2008/0318305 A1 | 12/2008 | Angros |
| 2009/0004691 A1 | 1/2009 | Erickson et al. |

FOREIGN PATENT DOCUMENTS

| | | |
|---|---|---|
| EP | 1691185 | 8/2006 |
| WO | WO 99/63324 | 12/1999 |
| WO | WO 03/106033 | 12/2003 |
| WO | WO 2009/127394 | 10/2009 |

AUTOMATED SYSTEMS AND METHODS FOR PREPARING BIOLOGICAL SPECIMENS FOR EXAMINATION

CROSS-REFERENCE TO RELATED APPLICATIONS

This application claims priority under 35 U.S.C. §119(e)(1) to U.S. Provisional Patent Application No. 61/460,775, filed on Nov. 10, 2010, and to U.S. Provisional Patent Application No. 61/510,180, filed on Jul. 21, 2011. The contents of each of the foregoing applications are incorporated by reference in their entirety.

BACKGROUND

For years, laboratory technologists have used dyes and stains such as those used in Romanowsky staining for preparing biological specimens to improve the contrast of a specimen during examination. Such examination typically utilizes a microscope, another device that captures images of the specimen, or, in other instances, unaided visual examination. Several different systems and methods for preparing a specimen for examination are known. For example, U.S. Pat. Nos. 6,096,271; 7,318,913; and 5,419,279, and published U.S. Patent Application Nos. 2008/0102006 and 2006/0073074 relate to machines and methods for staining a substrate during specimen processing. These publications provide various details on staining and preparing specimens for examination.

SUMMARY

The present disclosure relates to automated systems and methods for preparing biological specimens for examination. The specimens can include, for example, a blood sample containing red blood cells, white blood cells, and platelets, applied to a substrate, e.g., a microscope slide or a cover slip. Different embodiments can be used to prepare other biological specimens from biological samples including bone marrow, urine, vaginal tissue, epithelial tissue, tumors, semen, saliva, and other body fluids. Additional aspects of the disclosure include systems and methods for fixing, staining, rinsing, and agitating the specimens. In general, the systems and methods disclosed herein provide for rapid, efficient, and highly uniform specimen processing using minimal fluid quantities. The methods include one or more fixing, staining, and rinsing phases, including one or multiple agitation phases during or after one or more of the fixing, staining, and rinsing phases. The systems can be implemented as a standalone device or as a component in a larger system for preparing and examining biological specimens.

In general, in a first aspect, the disclosure features an apparatus for preparing a biological specimen on a substrate for examination, the apparatus including: (a) a substrate arm including a substrate gripper; (b) a first actuator connected to the substrate arm and configured to move the substrate arm between an open position and a specimen processing position; (c) a second actuator arranged and configured to agitate a substrate gripped by the substrate gripper on the substrate arm; (d) a platform having a top surface located opposite the substrate when the substrate arm is in the specimen processing position; and (e) two or more offsets arranged on the top surface of the platform such that when the substrate contacts all of the offsets in the substrate processing position, the substrate and top surface of the platform are substantially parallel and form a separation of at least about 50 microns.

Embodiments of the apparatus can include any one or more of the following features individually or in combination.

The first and second actuator can be the same actuator configured to both move the substrate arm and to agitate a substrate gripped by the substrate gripper on the substrate arm. A total surface area of the top surface of the platform can be smaller than a total surface area of the substrate. There can be at least three or more offsets arranged at outer edges of the top surface of the platform, where tips of the offsets define a plane.

A suction port can be located on the substrate gripper; the suction port can be connected to a suction source for providing suction to the suction port through a suction tube, to thereby hold the substrate to the substrate gripper. The apparatus can include a first stain port located on the top surface of the platform, a first stain reservoir, and a first stain conduit connected to the first stain port for providing a fluid pathway for stain to be pumped from the first stain reservoir to the first stain port and into the separation. The apparatus can include a second stain port located on the top surface of the platform at a location different from the first stain port location, a second stain reservoir, and a second stain conduit, where both the first and second stain ports are arranged on the top surface at a spacing from a specimen area on the substrate when the substrate is in the specimen processing position, and where the second stain conduit is connected to the second stain port to provide a fluid pathway for stain to be pumped from the second stain reservoir to the second stain port and into the separation.

The apparatus can include a first fixative port located on the top surface of the platform, a fixative reservoir, and a fixative conduit connected to the first fixative port for providing a fluid pathway for fixative to be pumped from the fixative reservoir to the first fixative port and into the separation. The apparatus can include a first rinse port located on the top surface of the platform, a rinse solution reservoir, and a rinse tube connected to the first rinse port for providing a fluid pathway for rinse fluid to be pumped from the rinse solution reservoir to the first rinse port and into the separation.

The apparatus can include a first vacuum port located on the top surface of the platform, a first waste container, and a first waste conduit connected to the first vacuum port for providing a pathway of negative pressure to evacuate fluid from the separation or substrate and deposit the fluid into the first waste container. The apparatus can include a second vacuum port located on the top surface of the platform and a second waste conduit connected to the second vacuum port for providing a pathway of negative pressure to evacuate fluid from the separation or substrate and deposit the fluid into the first waste container. The first and second vacuum ports can be located on opposite ends of the top surface of the platform.

The platform can include: a fixative port; a first stain port; a second stain port; a rinse port; a first vacuum port; and a second vacuum port. The apparatus can include a block arranged to support the platform, where the block includes: a fixative port; a first stain port; a second stain port; a rinse port; a first vacuum port; and a second vacuum port, where each port on the block is in a location corresponding to a port located in the platform.

The apparatus can include: a first stain reservoir; a second stain reservoir; a fixative reservoir; a rinse solution reservoir; a waste container; a pump; a plurality of fluid conduits connected to the pump and to the reservoirs and arranged for dispensing fluid from any one or more of the reservoirs; and a vacuum source for evacuating fluid from the substrate into the waste container. The apparatus can include a dryer positioned to direct a flow of air across the specimen when the substrate is located in the open position.

Embodiments of the apparatus can also include any of the other features, and any combinations of features, disclosed herein, as appropriate.

In a further aspect, the disclosure features methods of preparing a biological specimen on a substrate for examination that include: (a) positioning the substrate with respect to a surface so that the biological specimen faces the surface, and so that the substrate and the surface are substantially parallel and form a separation of at least about 100 microns; (b) sequentially dispensing (i) a first fixative solution, (ii) a first stain solution, (iii) a second stain solution, and (iv) a first rinse solution into the separation between the substrate and the surface in an amount sufficient to contact the specimen and the surface; and (c) after dispensing each one of solutions (i), (ii), (iii), and (iv) in step (b), and before dispensing the next one of solutions (i), (ii), (iii), and (iv) in step (b), performing at least a first agitation cycle, where the first agitation cycle includes changing the distance between the substrate and surface while the dispensed solution contacts the specimen for the duration of the first agitation cycle, and removing the dispensed solution from the separation and from contacting the specimen.

Embodiments of the methods can include any one or more of the following features.

Each sequential dispensing step can include dispensing one of the solutions in step (b) at a flow rate of at least 70 microliters per second for no more than three seconds. The first agitation cycle can include increasing the distance between the substrate and the surface by at least ten microns, and decreasing the distance between the substrate and the surface by at least five microns. Removing the dispensed solution can include applying a pressure of at least one pound per square inch less than an atmospheric pressure to the separation for at least two seconds.

Embodiments of the methods can also include any of the other features disclosed herein, and any combination of features, as appropriate.

In another aspect, the disclosure features methods of preparing a biological specimen on a substrate for examination, where the methods include: (a) positioning the substrate with respect to a surface so that the biological specimen faces the surface, and so that the substrate and the surface are substantially parallel and form a separation of at least about 50 microns; (b) dispensing a first stain into the separation between the substrate and the surface in an amount sufficient to contact the specimen and the surface; (c) performing at least a first agitation phase, wherein the first agitation phase includes changing the distance between the substrate and surface while the first stain is contacting the specimen for the duration of the first agitation phase; and (d) removing the first stain from the separation and the specimen.

Embodiments of the methods can include any one or more of the following features.

The dispensing step can include dispensing the stain at a flow rate of at least 70 microliters per second for no more than three seconds. The agitation phase can include increasing the distance between the substrate and the surface by at least ten microns, and decreasing the distance between the substrate and the surface by at least five microns. Removing the stain can include applying a vacuum force of at least one pound per square inch to the first stain in the separation for at least two seconds.

The methods can include: dispensing a second stain into the separation between the substrate and the surface in an amount sufficient to contact the specimen and the surface; performing a second agitation phase, where the second agitation phase includes changing the distance between the substrate and surface while the second stain is contacting the specimen for the duration of the second agitation phase; and removing the second stain from the separation and the specimen.

Embodiments of the methods can also include any of the other features and/or steps disclosed herein, and any combinations thereof, as appropriate. In a further aspect, the disclosure features methods of preparing a biological specimen on a substrate for examination, where the methods include: (a) positioning the substrate with respect to a surface so that the specimen faces the surface, and so that the substrate is positioned to form a separation between the surface and at least a portion of the substrate of at least about 50 to 250 microns, e.g., 50, 60, 65, 70, 75, 80, 85, 90, 95, 100, 125, 150, 175, 200, 225, or 250 microns; (b) performing a fixing phase that includes (i) dispensing a fixative into the separation between the substrate and the surface in an amount sufficient to contact the specimen and the surface, (ii) performing at least a first agitation phase, where the first agitation phase includes changing the distance between the substrate and surface while the fixative is contacting the specimen for the duration of the first agitation phase, and (iii) removing the fixative from the separation and the specimen; (c) performing a first staining phase that includes (i) dispensing a first stain into the separation between the substrate and the surface in an amount sufficient to contact the specimen and the surface, (ii) performing at least a second agitation phase, where the second agitation phase includes changing the distance between the substrate and surface while the first stain is contacting the specimen for the duration of the second agitation phase, and (iii) removing the first stain from the separation and the specimen; (d) performing a second staining phase that includes (i) dispensing a second stain into the separation between the substrate and the surface in an amount sufficient to contact the specimen and the surface, (ii) performing at least a third agitation phase, where the third agitation phase includes changing the distance between the substrate and surface while the second stain is contacting the specimen for the duration of the third agitation phase, and (iii) removing the second stain from the separation and the specimen; and (e) performing a first rinse phase that includes (i) dispensing a first rinse into the separation between the substrate and the surface in an amount sufficient to contact the specimen and the surface, (ii) performing at least a fourth agitation phase, where the fourth agitation phase includes changing the distance between the substrate and surface while the first rinse is contacting the specimen for the duration of the fourth agitation phase, and (iii) removing the first rinse from the separation and the specimen.

Embodiments of the methods can include any one or more of the following features.

The methods can include performing a second rinse phase, where the second rinse phase includes: (i) dispensing a second rinse into the separation between the substrate and the surface in an amount sufficient to contact the specimen and the surface; (ii) performing at least a fifth agitation phase, where the fifth agitation phase includes changing the distance between the substrate and surface while the second rinse is contacting the specimen for the duration of the fifth agitation phase; and (iii) removing the second rinse from the separation and the specimen. The methods can further include performing a drying cycle by directing a flow of air across the specimen.

The combined method steps can be performed, for example, in less than 70 seconds (e.g., in less than 60 seconds). In some embodiments, the methods can consume less than 650 microliters of fixative, first stain, second stain, and first rinse fluids. In certain embodiments, the methods can consume less than 850 microliters of fixative, first stain, second stain, first rinse, and second rinse fluids.

Embodiments of the method can also include any of the other features and/or steps, and any combinations thereof, disclosed herein, as appropriate.

In another aspect, the disclosure features automated specimen examination systems that include: an applicator station that applies a sample specimen to a substrate; any one of the biological specimen preparation apparatus disclosed herein; and an imaging station that images the biological specimen after preparation by the specimen preparation apparatus.

Embodiments of the automated specimen examination system can include any one or more of the features disclosed herein, as appropriate, including any one or more of the features of the biological specimen preparation apparatus' disclosed herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

Like reference symbols in the various drawings indicate like elements.

DETAILED DESCRIPTION

Disclosed herein are methods and systems for automated biological specimen processing. The automated specimen processing methods and systems described herein provide advantages over manual and other automated processing methods, including enhanced processing speed while using minimal reagent volumes and concurrently producing a highly uniform sample preparation that significantly reduces the variability associated with the application of stains, fixatives, and other reagents as compared to specimens processed by hand or by other systems.

Conventional automated processing methods typically have relatively high processing throughput while at the same time consuming large volumes of processing fluids, or have relatively low processing throughput while consuming reduced volumes of fluids. For many applications, however, both high throughput operation and low fluid consumption are desirable. By maintaining high throughput, specimens can be efficiently processed for subsequent examination. By keeping fluid consumption low, the amount of processing waste is reduced along with the required volume of processing reagents, keeping operating costs low. The systems and methods disclosed herein permit rapid automated processing of specimens (e.g., more than 100 specimens per hour by a single machine) using low volumes of processing fluids (e.g., less than 1 mL of fluids per specimen), while producing highly uniform and repeatable results.

Biological Specimen Preparation Systems and Methods

Figure 1:
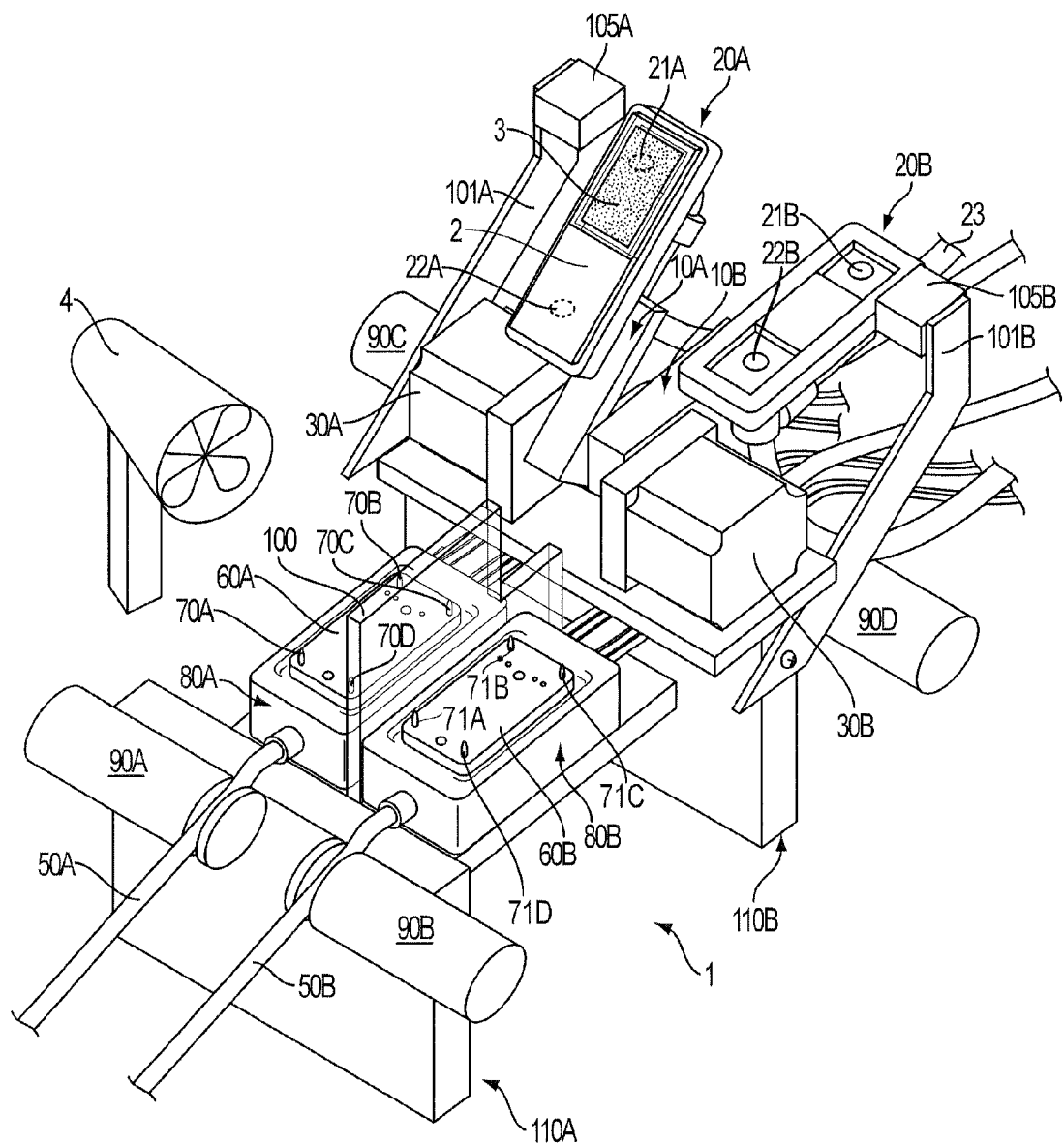
FIG. 1 is a perspective view of an embodiment of an apparatus for preparing biological specimens for examination, with both sample grippers 20A and 20B in an open position.

Before specimens are examined, they are prepared in a series of steps to enhance the visual appearance of certain features in the specimens. FIG. 1 illustrates an embodiment of an apparatus or machine 1 for preparing a biological specimen for examination or imaging on a substrate 2 such as a microscope slide, cover slip, or other transparent surface. Machine 1 can be incorporated into an overall system for preparing and analyzing specimens comprising body fluids or other biological samples containing cells, such as system 2000 shown in FIG. 15 and described below. Machine 1 can generally include, or form a portion of, a system that features a first station that obtains a specimen, a second station that applies the specimen to a substrate, third and fourth stations for fixing and staining the specimen, respectively, a fifth station that dries the specimen, a sixth station that images the specimen, and a seventh station for analyzing the images and data obtained from the specimen. Certain embodiments of machine 1 are compatible with system 2000; some embodiments of machine 1 can be used in other specimen preparation systems, and/or as stand-alone devices.

Figure 4:
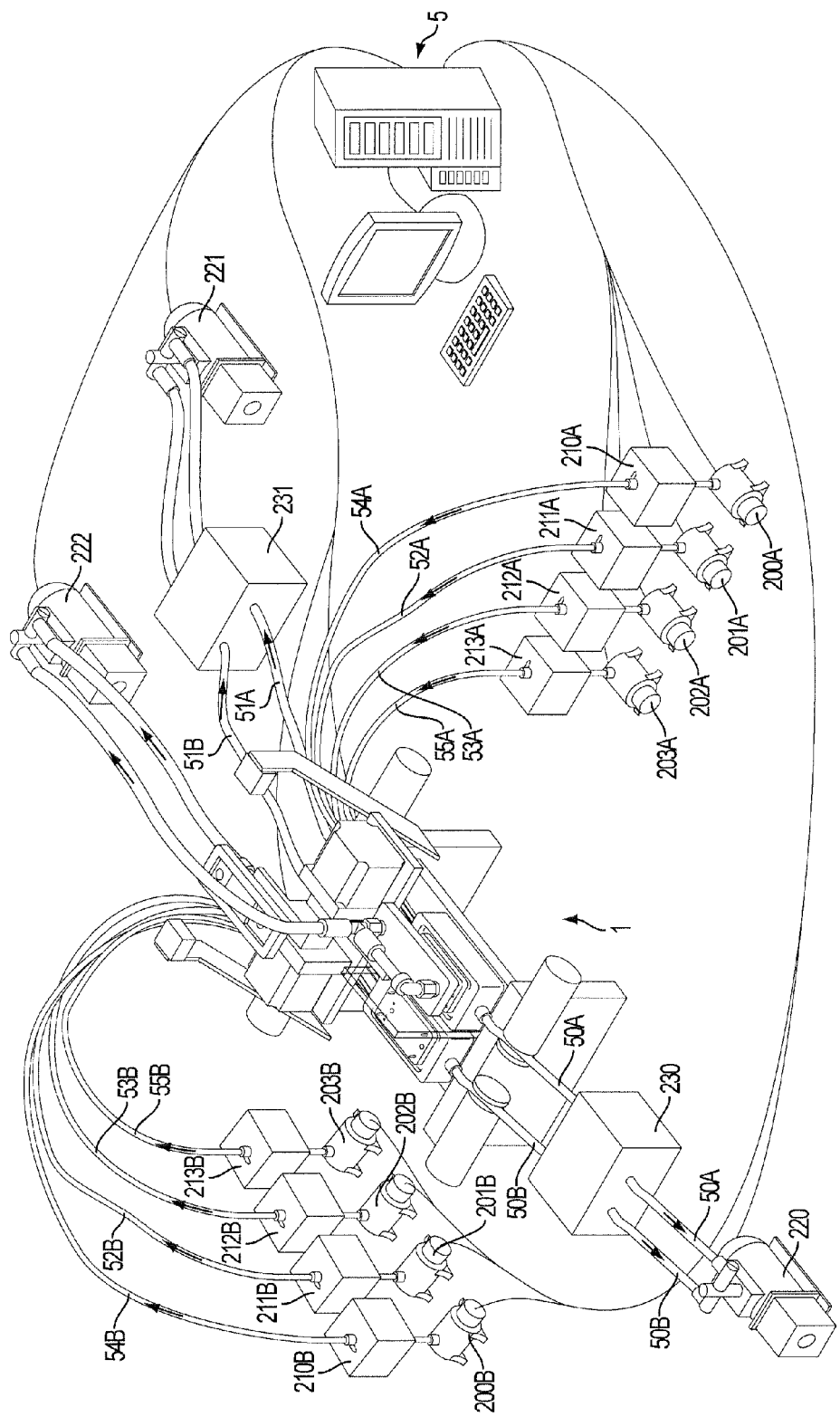
FIG. 4 is a perspective view of the apparatus of FIG. 1 showing connections between the apparatus and fluid reservoirs by means of multiple fluid conduits.

Machine 1 can include or connect to a control system 5 as shown in FIG. 4, which provides another perspective view of machine 1. Control system 5 can include one or more computers each containing a central processing unit capable of executing software instructions stored on computer readable media such as a hard drive, optical drive, or memory. Additionally, control system 5 can include electrical circuitry for executing the software instructions. Control system 5 can include a user interface for receiving user commands to control the operation of machine 1. Software stored on or provided to the computer can include programs that control the operation of components of machine 1 during specimen processing, such as fluid pumps and vacuums. For example, the software can include instructions for directing the machine 1 to apply various fixatives, stains, and rinses to the specimen, and to perform several agitation steps during specimen processing.

In addition, the software can include default settings, and the user interface may contain customization features for providing the user with the ability to change these defaults settings. For example, the user interface can contain customization features for allowing a user to customize the speed, frequency, or order of fixing, staining, and rinsing phases, as well as agitation parameters (further described below). Control system 5 can also communicate via a network protocol (such as Appletalk®, IPX, or TCP/IP). For example, the network protocol may use cables (such as twisted pair cables) and/or a wireless connection such as WiFi. The control system may be connected to a laboratory information system using the network protocol. The laboratory information system can contain a server and/or database for storing information relating to specimens processed on machine 1. For example, the database may contain a table that provides information about the person or source of the specimen (e.g., name, date of birth (DOB), address, time specimen was taken, gender, etc.), information relating to processing of specimen (processed on date ##/##/####, specimen number #, etc.), a copy of any images acquired of the specimen, and copies of any results obtained by analyzing the images.

Referring to FIG. 1, machine 1 can include supports 110A and 110B to secure the device to a location within a system or a laboratory workstation. Machine 1 also includes one or more substrate arms 10A and 10B, each connected at their base to an actuator 30A and 30B. The opposite ends of the substrate arms 10A and 10B include substrate grippers 20A and 20B for receiving and holding substrates during specimen processing. Each substrate gripper 20A and 20B receives and holds a substrate 2 while machine 1 completes all specimen processing steps (described below). The substrate may be or include a microscope slide, a cover slip, or other transparent material suitable for holding a specimen during specimen processing and microscopic examination after specimen processing. The embodiment of FIG. 1 depicts a glass microscope slide, substrate 2, which includes a biological specimen 3. Using suction ports, substrate grippers 20A, 20B can hold the substrate 2 to substrate arms 10A, 10B during specimen processing. A suction tube 23 provides suction to the substrate grippers 20A and 20B through suction ports 21A and 21B, and 22A and 22B (note that ports 21A and 22A are positioned behind the slide 2 in FIG. 1, and are shown in dashed lines).

Figure 2:
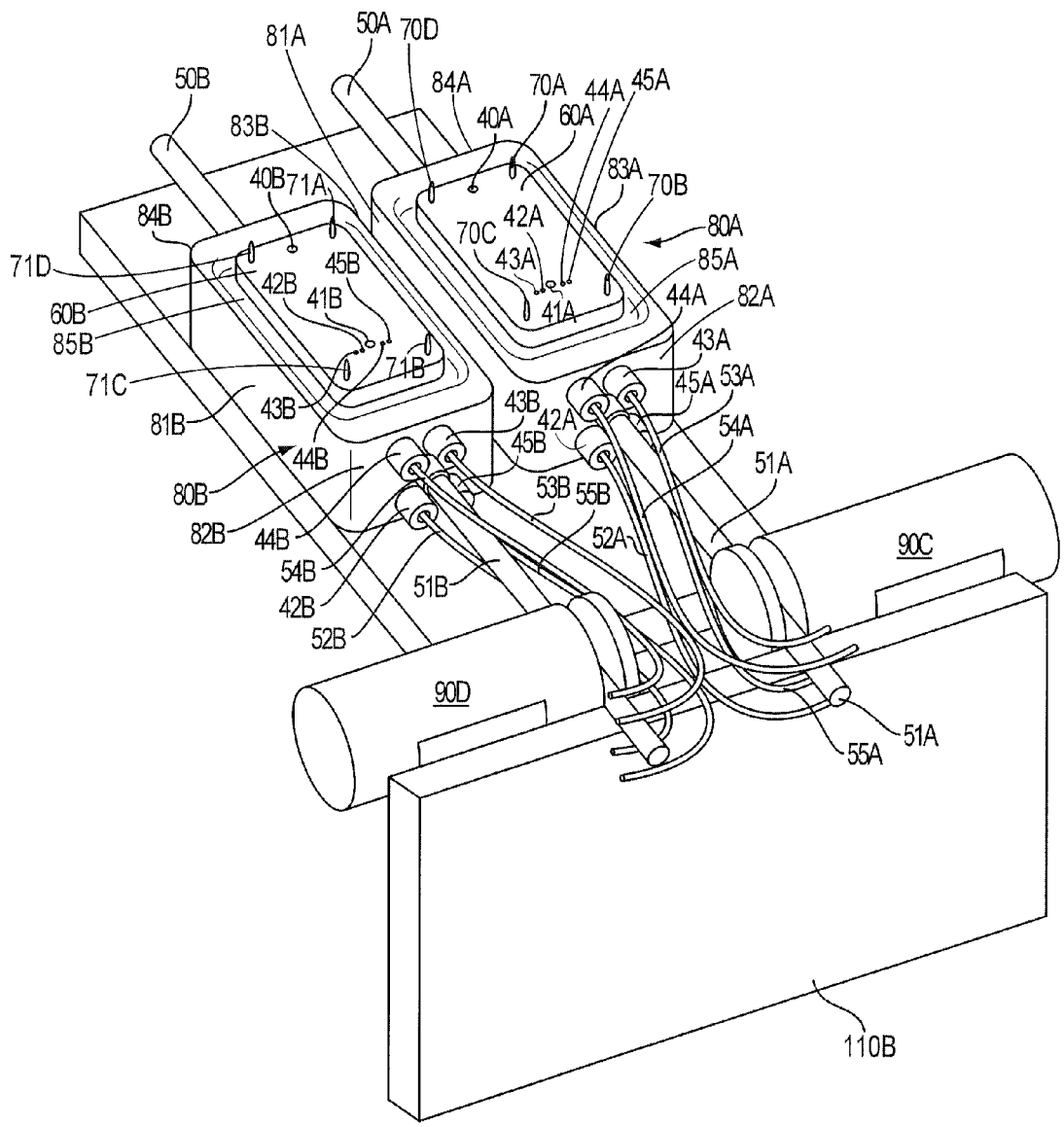
FIG. 2 is another perspective view of a portion of the apparatus of FIG. 1 (with the substrate arms and sample grippers not shown).

The machine 1 embodiment shown in FIGS. 1-3 is a dual substrate machine, capable of holding and processing a substrate on each of substrate arms 10A and 10B. Other embodiments provide for processing a single substrate or three or more substrates, sequentially or simultaneously. Further, while the embodiments depicted in FIGS. 1-6 use suction to attach the substrates 2 to the substrate arms 10A and 10B, alternative embodiments can use various types of clamps, fingers, or magnets (if the substrate is magnetized) to attach a substrate 2 to a substrate arm 10A during specimen processing.

Figure 5:
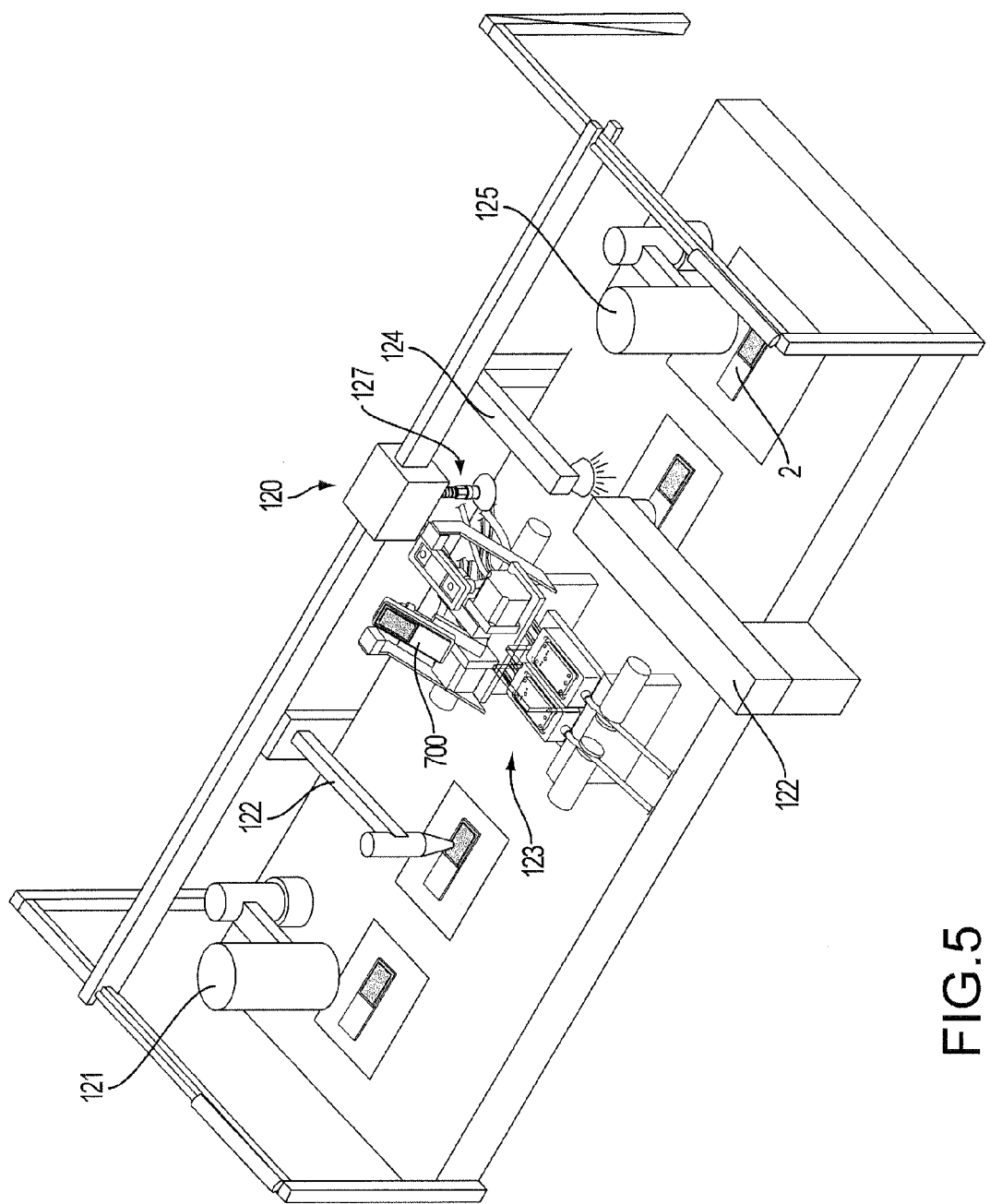
FIG. 5 is a perspective view of a specimen examination system that includes an automated substrate mover and an embodiment of a specimen preparation apparatus as described herein.
Figure 18A:
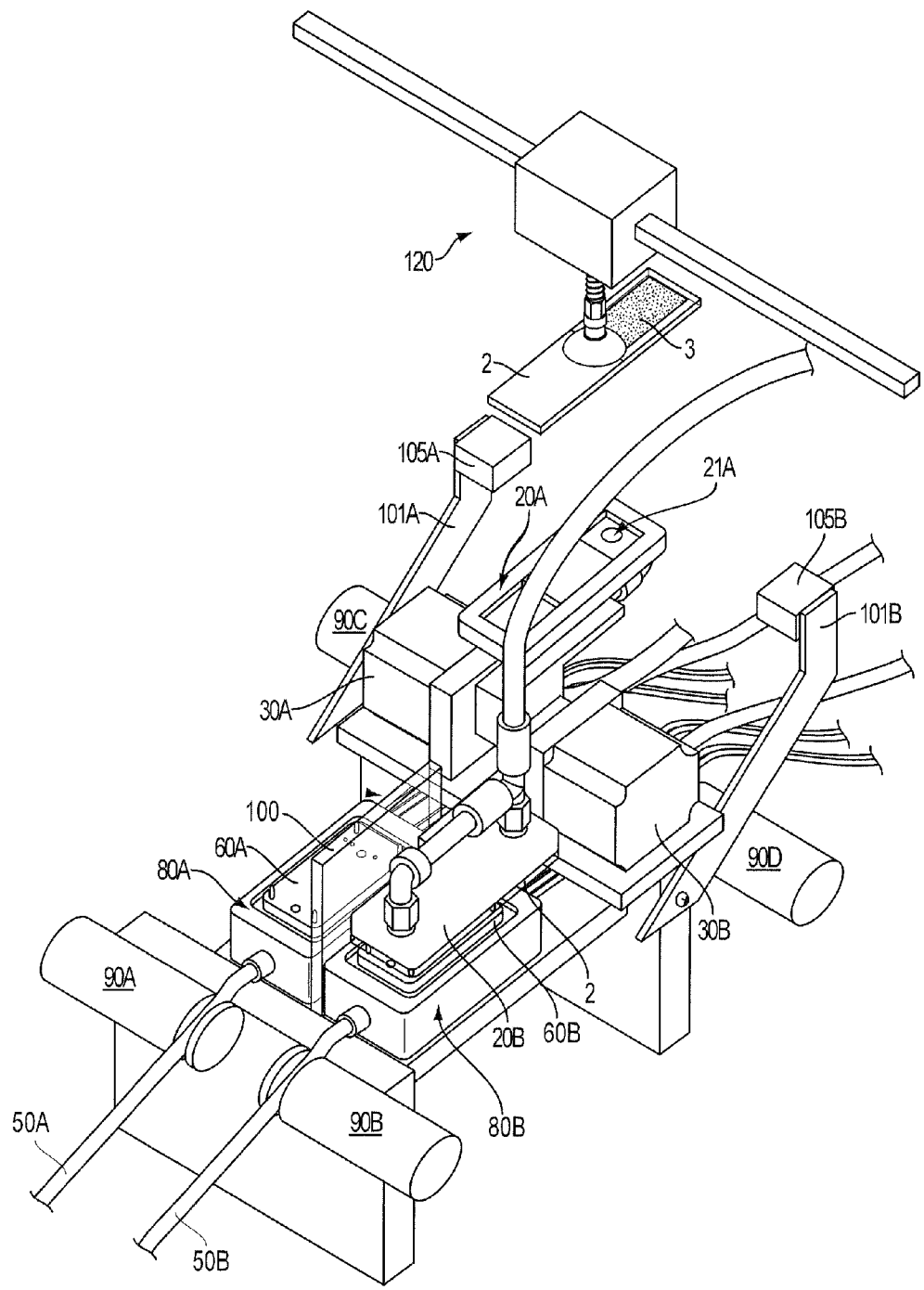
FIGS. 18A and 18B are perspective views of the apparatus of FIG. 1 that show placement of a substrate onto a substrate arm by an automated substrate mover.
Figure 18B:
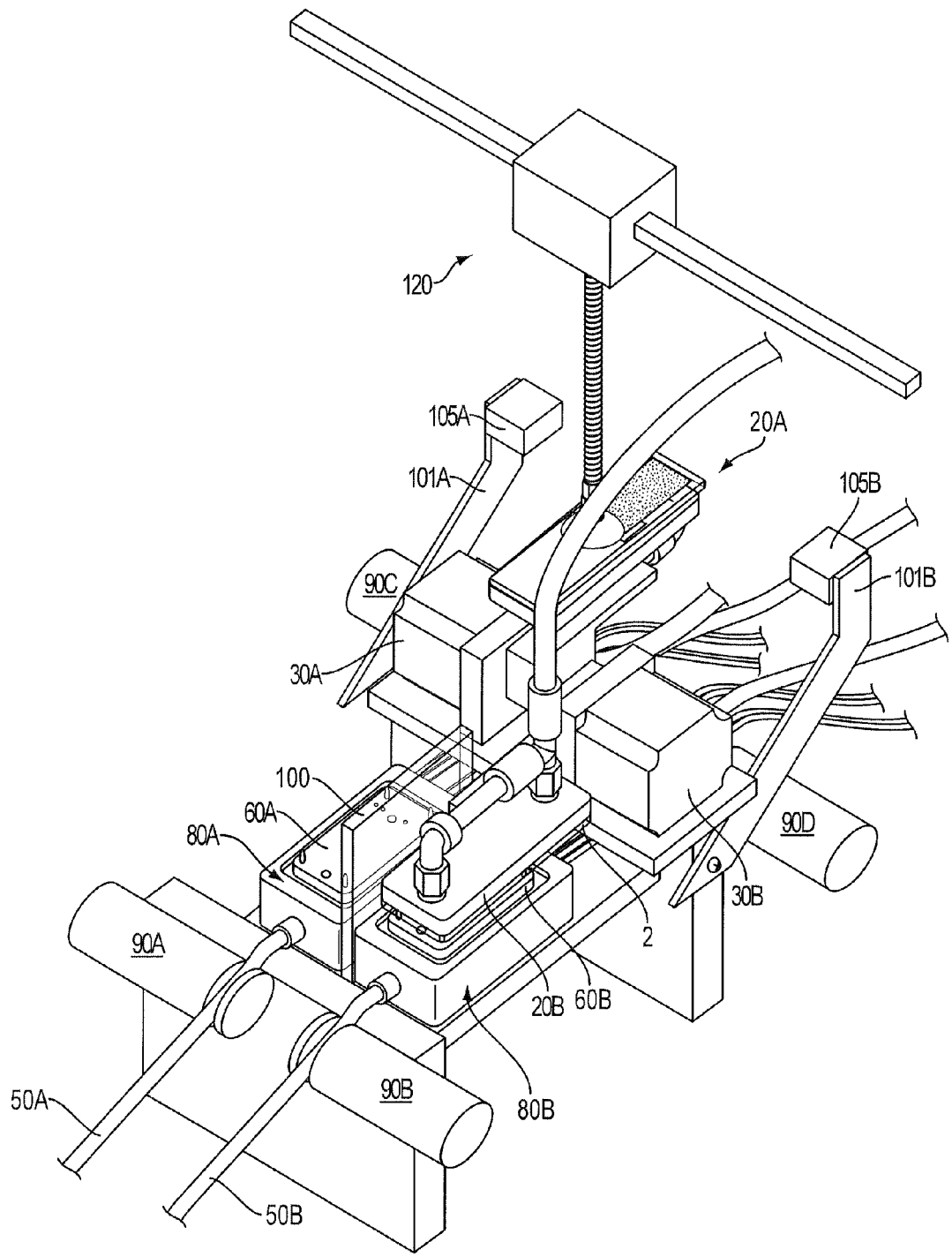

In the embodiments shown in FIGS. 5 and 18A-B, machine 1 receives a substrate 2 carrying a specimen 3 from an automated substrate mover 120 or manually from an individual. As an example, the substrate mover 120 can be a device that transports a substrate between stations (e.g., station 121 to station 122 to station 123, to station 124, and to station 125). FIG. 5 shows a system having a first label reader station 121, an applicator station 122, a staining station 123 that includes machine 1, a camera or imaging station 124, and a second label reader station 125. The first label reader station 121 is configured to read information from substrate 2 such as a bar code and/or "fingerprint" information that is used to identify the particular substrate 2 and specimen 3 thereon. The second label reader station 125 functions in the same manner, and the information it reads is used to verify that the specimen 3 that is imaged at station 124 is the same as the substrate that was processed.

Substrate mover 120 can include a gripper 127 for holding the substrate 2, and registration circuitry or software to enable the mover 120 to determine whether the substrate 2 is mounted in the mover 120. In one embodiment, substrate mover 120 can include a hydraulic cylinder for moving substrate 2 from a first station 121 to a second station 122. After specimen processing, the substrate mover 120 may remove the processed substrate from staining station 123 and transport the substrate 2 to another station for substrate examination, such as a microscope or station 124. Alternatively, an individual may manually remove a substrate from machine 1 after specimen processing.

Figure 7A:
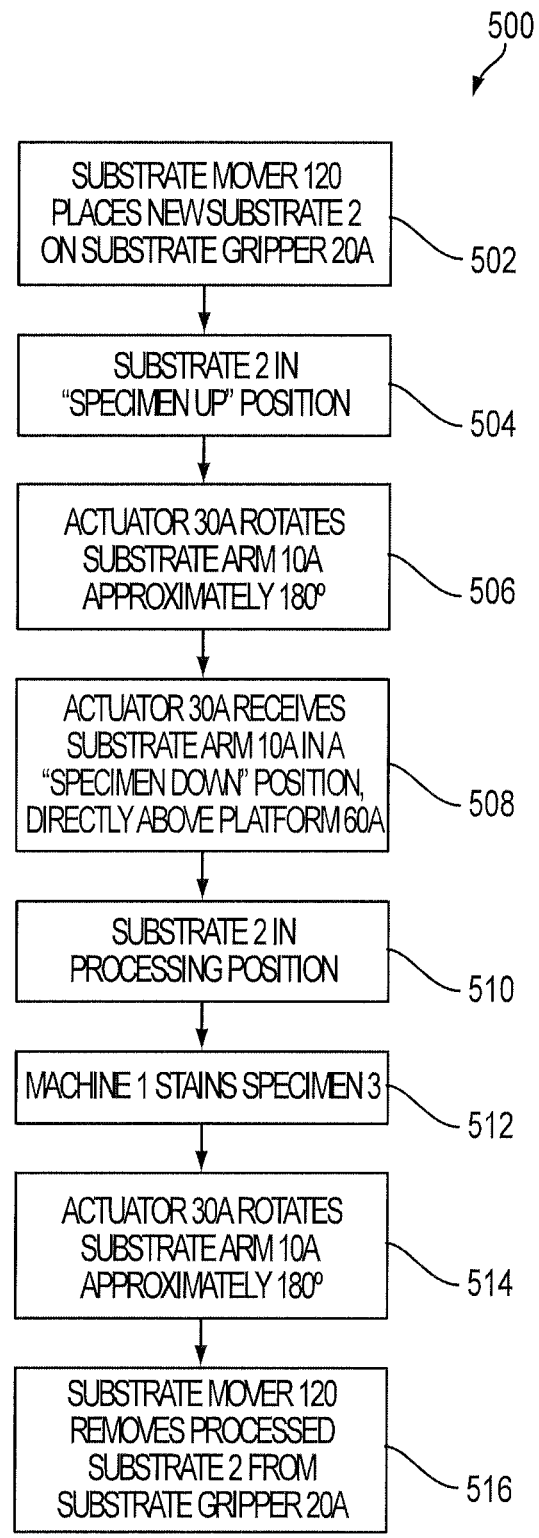
FIG. 7A is a flow chart showing a series of steps for moving substrate arms from an open position to closed (specimen processing) position.
Figure 7B:
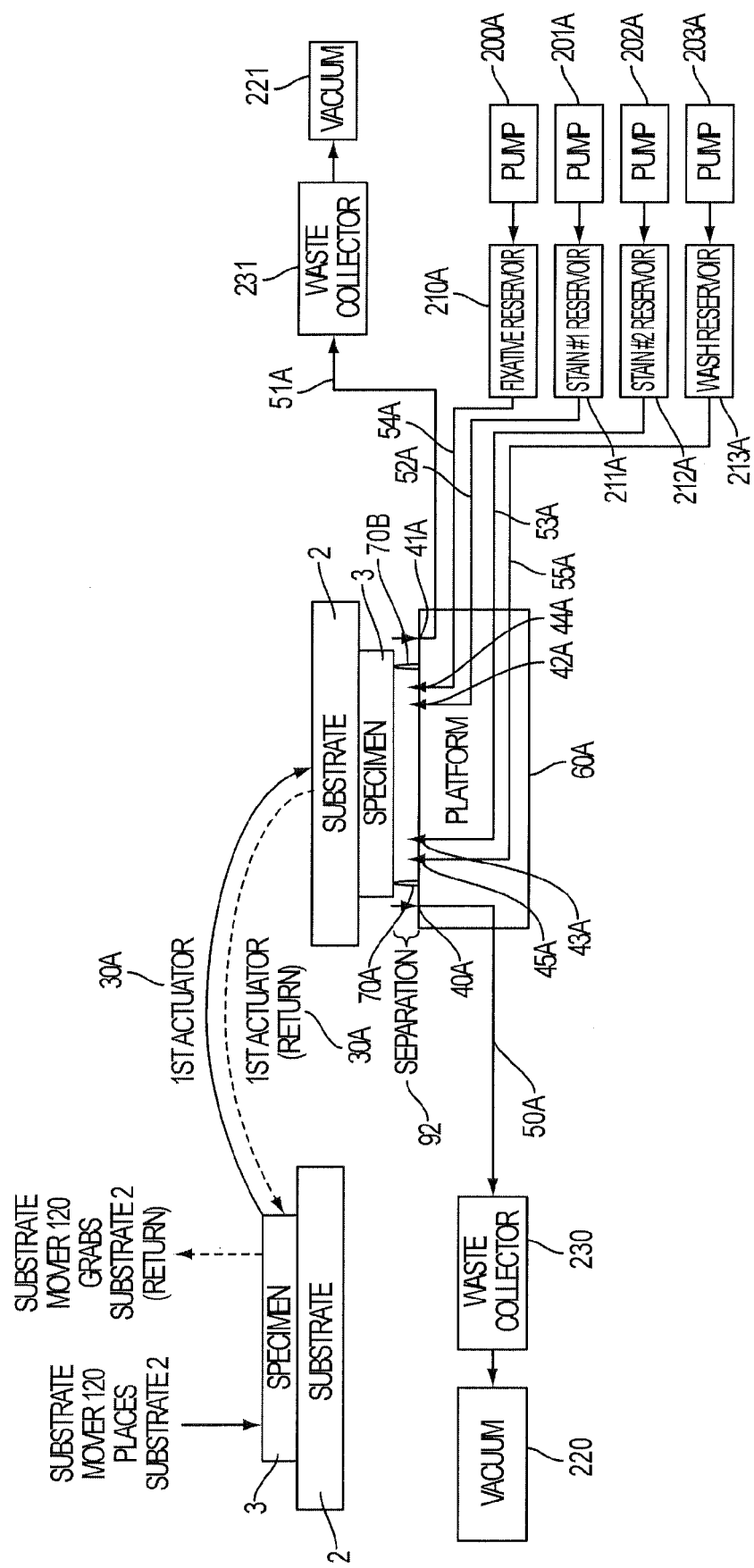
FIG. 7B is a schematic diagram of an embodiment of a specimen preparation apparatus as described herein.

The substrate arms 10A and 10B can rotate about an axis to enable the substrate to move from an open position for loading, to a specimen processing position, and back to the open position for unloading after specimen processing. FIG. 7A shows a flow chart 500 that includes a series of steps for moving substrate arms from an open position to a processing position. Flow chart 500 is further described below with reference to FIG. 7B, which shows a schematic diagram of machine 1.

Note that machine 1 in FIG. 1 is configured to accept and examine two substrates. In the following discussion and figures, reference may be made to only one set of components in machine 1 (e.g., substrate gripper 20A, actuator 30A, substrate arm 10A, etc.). However, it is to be understood that the same steps, features, and attributes that are disclosed in connection with one set of components can also apply to the other set of components in machine 1 (e.g., substrate gripper 20B, actuator 30B, substrate arm 10B, etc.). Thus, while the discussion herein focuses only on one set of components for clarity and brevity, it is understood that machines for specimen examination such as machine 1 can include two or more than two sets of components, each set having some or all of the features discussed herein.

Returning to FIGS. 7A and 7B, in a first step 502 of flow chart 500, substrate mover 120 places a substrate 2 in contact with a substrate gripper 20A. In step 504, substrate 2 is positioned on the substrate gripper in a "specimen up" or "open" position. Next, in step 506, actuator 30A rotates substrate arm 10A by approximately 180° (see FIG. 7B) to position substrate 2 in a "specimen down" or "specimen processing" or "closed" position (step 508), directly above platform 60A, so that substrate 2 is in a processing position in step 510.

Then, in step 512, machine 1 stains specimen 3 positioned on substrate 2 by directing suitable fluids including stains, wash fluids, and fixatives to be pumped from reservoirs 210A, 211A, 212A, and 213A into contact with specimen 3 through ports 42A, 43A, 44A, and 45A. Excess fluids are removed from specimen 3 by vacuum pumping through ports 40A and 41A, and are collected in waste collectors 230 and 231.

In step 514, following staining of specimen 3, actuator 30A rotates substrate arm 10 by approximately 180° (reversing the rotation of step 506) to return the substrate to the "specimen up" position. Finally, in step 516, substrate mover 120 removes the processed substrate from substrate gripper 20A. Other open or "specimen up" positions can also be used, provided that an operator or automated substrate mover can load and unload substrates from machine 1. For example, the specimen up position can be rotated 100° or more (e.g., 120° or more, 130° or more, 140° or more) from the specimen processing position. In some embodiments, the specimen up position can be rotated less than 100° (e.g., less than 90°, less than 80°, less than 70°) from the specimen processing position, provided that an operator or substrate mover can load and unload substrates from machine 1.

Actuators 30A and/or 30B may include an electric motor, pneumatics, magnetic systems, or other hardware (e.g., a worm gear) to move arm 10A and/or 10B. When substrate arms 10A and 10B are in an open position as depicted in FIG. 1, grippers 20A and 20B can each receive a substrate 2. Once loaded onto a substrate gripper 20A or 20B, actuators 30A and/or 30B then rotate arms 10A and/or 10B, and thus substrate 2, from the open ("specimen up") position to a processing position ("specimen down," as shown for arm 10B in FIG. 3A) for application of fixative, stain, and rinse solutions, including agitation steps, and back to an open position for unloading after processing.

Figure 3A:
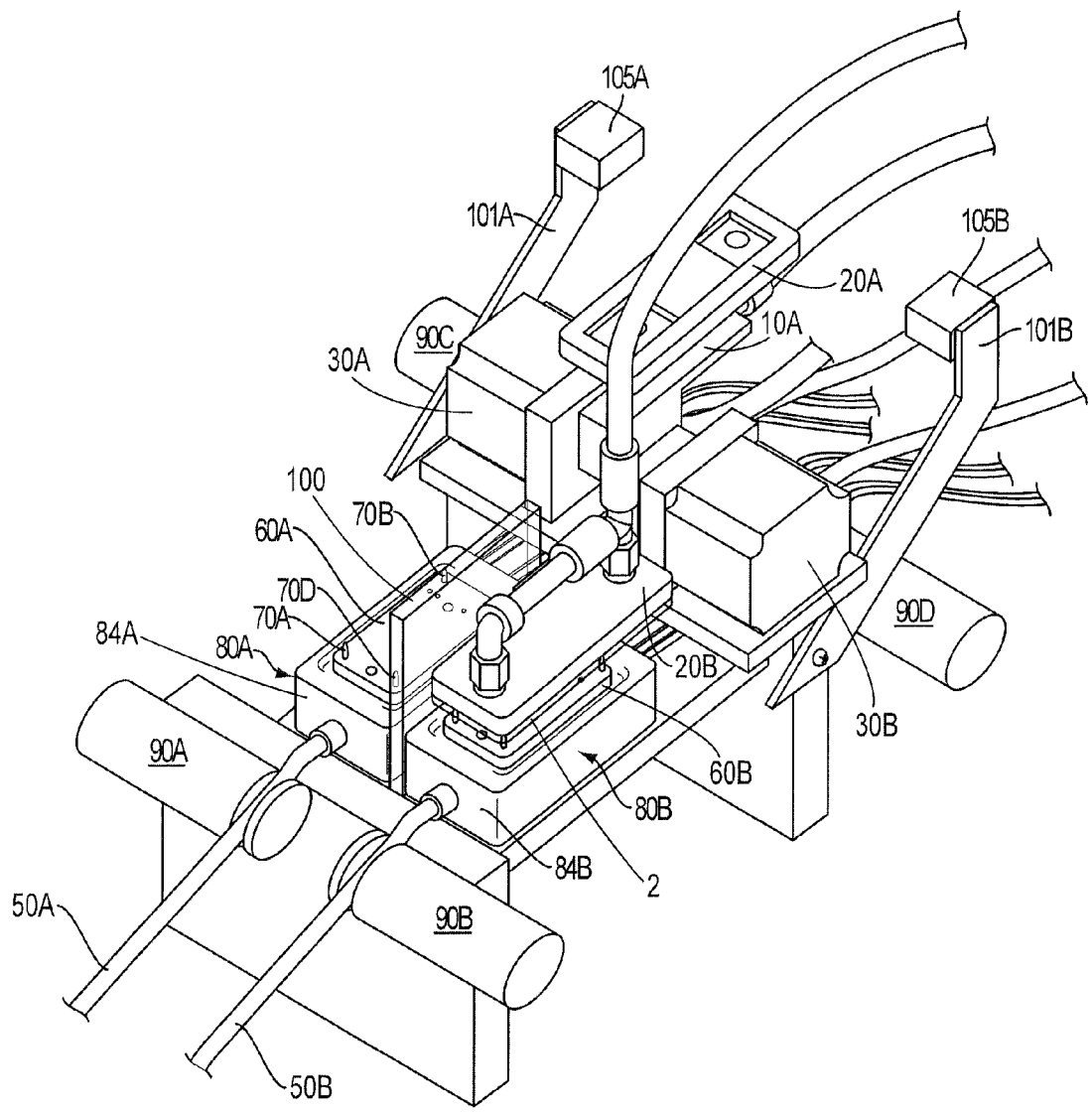
FIG. 3A is a further perspective view of the apparatus of FIG. 1, with sample gripper 20A in an open position and sample gripper 20B in a closed (specimen processing) position.

With reference to FIG. 3A, actuator 30B has rotated substrate arm 10B from the open position depicted in FIG. 1 to a "closed" or processing position. FIG. 3A shows that the substrate 2 on substrate arm 10B has been flipped over and rotated approximately 180° from its loading position shown in FIG. 1 to a downward-facing position where specimen 3 on substrate 2 is substantially parallel to the surface of platform 60B. As discussed in connection with FIG. 7A above, while substrate 2 is positioned proximal to platform 60B in the specimen processing position shown, machine 1 applies various fixatives, stains, and rinses to specimen 3 on substrate 2 through several processing phases, which will be described in greater detail below. To remove substrate 2 from the processing position, actuator 30B rotates substrate arm 10B back to the open position shown in FIG. 1 (both arms) and FIG. 3A (where only arm 10A is in the open position).

In certain embodiments, control system 5 can detect the position of the arms utilizing one or more sensors 105A and 105B to detect indicator arms 101A and 101B (as shown in FIGS. 1 and 3). Sensors 105A and 105B can be proximity sensors, e.g., photoelectric sensors, utilizing, e.g., infrared light or various other technologies (lasers, motion detectors, etc.) to detect the presence or absence of the arms. For example, proximity sensors 105A or 105B can have a detection field, and the sensors can determine whether or not a substrate arm (e.g., arm 10A and/or 10B) or a substrate gripper (e.g., gripper 20A and/or 20B) is within the detection field. Control system 5 can receive information from the sensors to determine the positions of substrate arms 10. For example, when substrate arm 10B (not shown in FIG. 3A) is rotated to a processing position, proximity sensor 105B on the proximal end of indicator arm 101B senses target substrate gripper 20B, and notifies control system 5 that substrate arm 10B is rotated to a specimen processing position. In this position, proximity sensor 105B on the distal end of indicator arm 101B will not send a signal to control system 5, because the sensor does not detect any target (e.g., a substrate arm or substrate gripper).

When substrate arm 10B rotates to an open position (as shown in FIG. 1), proximity sensor 105B on the distal end of indicator arm 101B senses target substrate gripper 20B, and notifies control system 5 that substrate arm 10B is rotated to an open position. Stated differently, when substrate arm 10B has rotated away from the sensor 105B, the sensors send a "not present" signal to the control system 5. When arm 10B is rotated into the open position, arm 10B is closer to the sensor 105B, and the sensor can send a "present" signal to the control system 5. In alternate configurations, the sensor can be mounted on substrate 10B and can detect the presence of the indicator arm 101B. In some embodiments, control system 5 can be used to calibrate the position of actuators 30A and 30B to known open and specimen processing positions, and/or to actively monitor the movement and position of substrate arms 10A and 10B based on control signals and/or feedback received from actuators 30A and 30B.

Figure 8A:
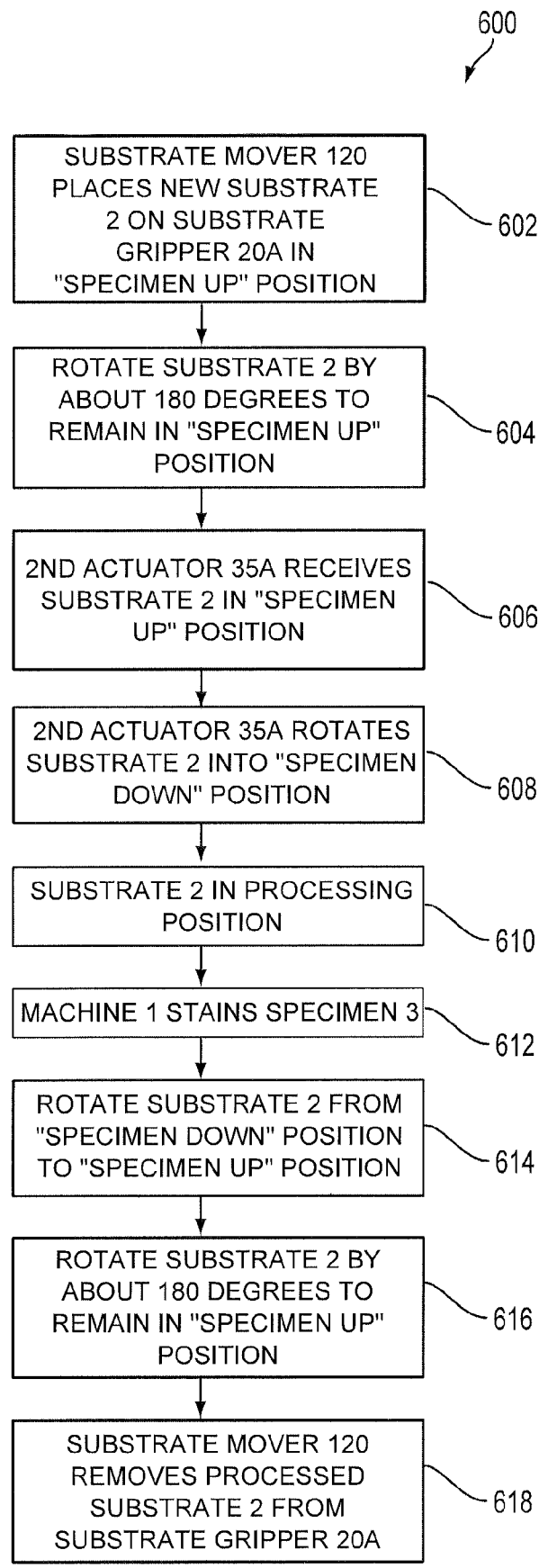
FIG. 8A is a flow chart showing an alternate series of steps for moving substrate arms from an open position to a specimen processing position.
Figure 8B:
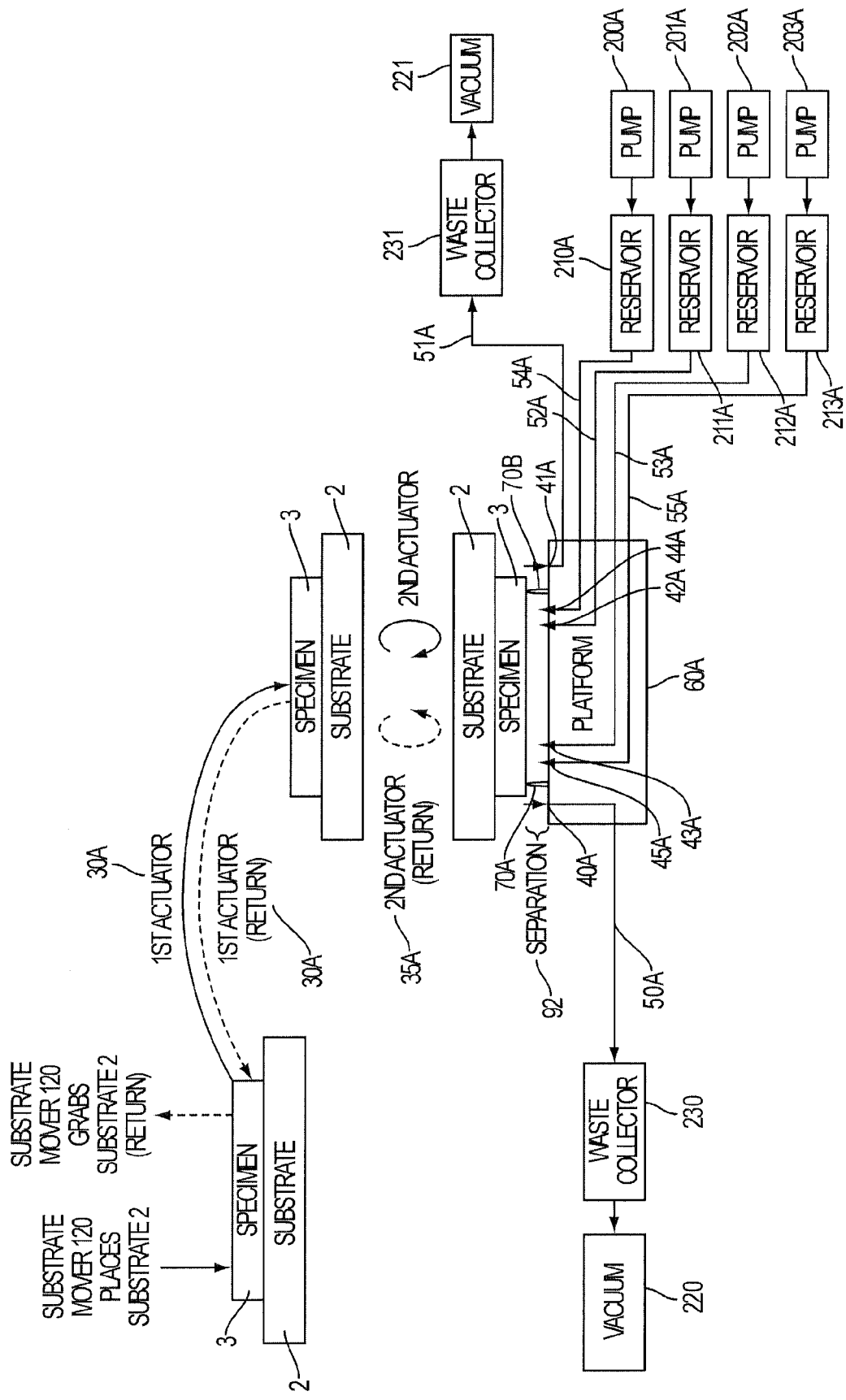
FIG. 8B is a schematic diagram of an apparatus for preparing biological specimens for examination that includes two actuators.

The structure and axis of rotation for substrate arms 10A and 10B in FIG. 1 may be varied in other embodiments of the invention. FIG. 8A shows a flow chart 600 that includes an alternate series of steps for moving substrate arms from an open position to a processing position. Flow chart 600 is further described below with reference to FIG. 8B, which shows a schematic diagram of machine 1.

In step 602 of flow chart 600, substrate mover 120 places substrate 2 on substrate gripper 20A in a "specimen up" orientation. Then, in step 604, a first actuator 30A rotates substrate 2 by approximately 180° in a plane perpendicular to the plane of FIG. 8B, so that substrate 2 remains oriented in a "specimen up" position above platform 60A. In step 606, a second actuator 35A receives substrate 2 oriented in the "specimen up" position. Then, in step 608, second actuator 35A (e.g., positioned between substrate arm 10A and substrate gripper 20A) rotates the substrate 2 into a "specimen down" orientation. Second actuator 35A can also move substrate 2 downward toward platform 60A so that substrate 2 contacts offsets 70A and 70B.

Next, with substrate 2 in the processing position in step 610, machine 1 stains specimen 3 on substrate 2 by applying stains, fixatives, and wash solutions as discussed above in connection with step 512 of flow chart 500. After staining is complete, second actuator 35A rotates substrate 2 from a "specimen down" orientation to a "specimen up" orientation (step 614), and then first actuator 30A rotates substrate 2 by approximately 180° (e.g., in a plane perpendicular to the plane of FIG. 8B, reversing the rotation applied in step 606) so that the substrate remains oriented in a "specimen up" position. Finally, in step 618, substrate mover 120 removes the processed substrate from substrate gripper 20A.

In general, machine 1 may include one or more (e.g., two, three, four, five, or more than five) platforms 60A and 60B as shown in FIGS. 1-3 for specimen processing. As shown in FIG. 2, platform 60A can include lateral sides for supporting a top side of the platform. A shield 100, shown in FIGS. 1 and 3, can be positioned between the platforms 60A and 60B to prevent fluids from splattering between the platforms 60. In some embodiments, shield 100 can be formed from a transparent material that blocks fluids from one of platforms 60A and 60B from contaminating the other platform. In certain embodiments, shield 100 can be formed from a material that is translucent or opaque. In FIGS. 1 and 3, shield 100 is depicted as being formed from a transparent material to allow other components positioned behind shield 100 to be shown in the same figure. Shield 100 could also have been shown as being formed from an opaque material, in which case portions of some components such as platform 60A and block 80A would have been obscured.

Figure 3B:
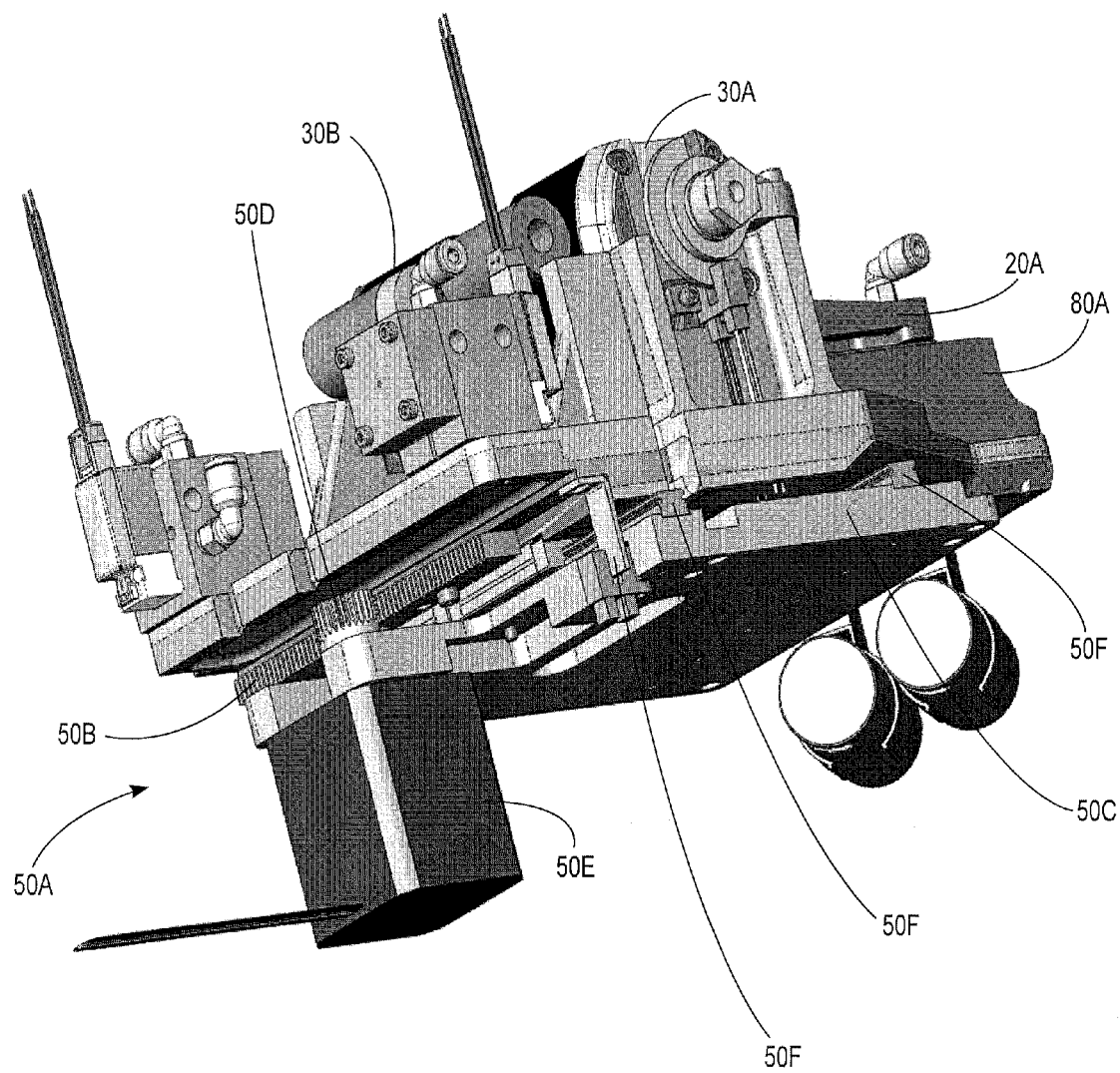
FIG. 3B is a perspective view of an indexing mechanism of the apparatus of FIG. 1.

FIG. 3B shows an indexing mechanism 50A that can be used to translate the machine 1 to provide substrates 2 from each of the substrate grippers 20A, 20B to a position for specimen processing. The indexing mechanism 50A can be in many forms, such as electromechanical devices (e.g., a rack and pinion gear set powered by an electric motor), linear actuators (e.g., pneumatic actuators, hydraulic actuators, or electromagnetic actuators). Although, in the illustrated embodiment, the indexing mechanism 50A translates the machine 1 linearly between two positions, other translation paths are possible based on the number of platforms included on the machine 1, and their configuration and layout, such as circular or semi-circular (e.g., an indexing table that can move in an arcuate path). As shown, the indexing mechanism 50A can include a gear rack 50B attached to a base 50C of the machine 1 and a pinion gear 50D attached to an electric motor 50E that is fixed to the base 50C. The machine 1 can be attached to the base 50C using one or more sliding devices 50F so that the machine 1 can move smoothly when translated by the indexing mechanism 50A. During use, the indexing mechanism 50A can move the machine 1 so that the multiple substrate grippers 20A and/or 20B of the machine 1 to receive a substrate 2 from a substrate mover 120 (shown in FIG. 5) so that a sample disposed on the substrate 2 can be prepared by the machine 1, and also so that, once prepared, the substrate gripper 20A and/or 20B can provide the substrate 2 having a prepared sample can be provided to the substrate mover 120 for sample processing.

For machines having two platforms 60A and 60B, as in the illustrated embodiment, substrates 2 are typically provided to, and from, the substrate mover 120 in an alternating manner. In some embodiments, a first substrate 2 is provided from the substrate mover 120 to a first substrate gripper 20A, to be processed at a first platform 60A, while the machine 1 is in a first position. While the first substrate 2 is processed at the first platform 60A, the indexing mechanism 50A can translate the machine 1 to a second position so that a second substrate gripper 20B can receive a second substrate, to be processed at the second platform 60B, from the substrate mover 120. While the second substrate is processed at the second platform 60B, the indexing mechanism 50A can translate the machine 1 back to the first position so that the substrate mover 120 can remove the first substrate 2 from the first substrate gripper 20A. Once the substrate 2 is removed from the first gripping platform 20A, a next substrate can be provided to the first gripping platform 20A. This method for providing substrates to alternating gripping platforms can be implemented for more than two (e.g., three, four, five, or more than five) platforms thereby increasing throughput of specimens prepared for further evaluation.

Platforms 60A and 60B are typically formed from one or more materials that are relatively chemically inert with respect to the fluids used during specimen processing and provide a suitable surface tension. Exemplary materials that can be used to form platforms 60A and 60B include engineering thermoplastics, such as polyoxymethylene (e.g., Delrin® manufactured by DuPont), high molecular weight fluorocarbons, such as polytetrafluoroethylene (PTFE) (e.g., Teflon® manufactured by DuPont), and metals such as aluminum, steel, and titanium, provided they are manufactured and/or treated to provide a suitable surface tension that acts to assist in evenly distributing and confining the processing fluids to the space between substrate 2 and the platforms, and allowing suitable evacuation of the processing fluids as well. By selection of suitable materials, the platforms can also advantageously reduce or minimize the formation of bubbles or spaces within the fluids as they are distributed, and at the same time maintain a sufficient surface tension such that fluid leakage out of the separation between the platforms and substrate 2 is reduced or eliminated.

In general, the surface area of platforms 60A and 60B can be selected as desired for purposes of substrate handling and fluid delivery. Factors such as the surface area of platforms 60A and 60B can also influence the selected surface area of substrate 2. For example, in some embodiments, the surface area of platform 60A (e.g., the area of the surface of platform 60A that faces substrate 2) is slightly smaller than the area of the surface of substrate 2 that faces platform 60A. By maintaining such a relationship between the areas of the facing surfaces of platform 60A and substrate 2, fluid leakage from the region between the surfaces can be reduced or eliminated. Typically, for example, the area of the surface of substrate 60A that faces substrate 2 is smaller than the area of the surface of substrate 2 by 2% or more (e.g., 3% or more, 5% or more, 7% or more, 10% or more, 15% or more, 20% or more, 25% or more, 30% or more).

Platforms 60A and 60B can be attached to blocks 80A and 80B, respectively. Block 80A includes lateral sides 81A-84A supporting a top side 85A as shown in FIG. 2. Blocks 80A and 80B can be made of the same or similar materials to those used for the platforms, including metals, ceramics, and/or plastics. Thus, materials such as Delrin® can be used to form blocks 80A and 80B, particularly in embodiments that implement Romanowsky staining of specimens. Other materials that can be used in embodiments include metals, and Teflon® brand polytetrafluoroethylene-coated aluminum, steel, or titanium.

In some embodiments, platforms 60A and/or 60B can be raised as shown in FIGS. 1-3. Alternatively, in certain embodiments, platforms 60A and/or 60B can be flush with the upper surface of blocks 80A and 80B, respectively. In either case, certain features of machine 1 as well as surface tension of fluids and surface energy of the platform or block prevent excess fluids from flowing past the edges of platforms 60A/60B and/or blocks 80A/80B.

As shown in FIGS. 1 and 2, platform 60A can include offsets 70A-70D to provide a separation between the surface of platform 60A and substrate 2, and prevent substrate 2 from contacting platform 60A. Platform 60B can include a corresponding set of offsets 71A-71D. Offsets can include standoffs, pins, pegs, rods, beads, walls, or other structures that provide separation between the surface of platform 60A and/or 60B and substrate 2. Offsets 70A-70D and 71A-71D ensure that the surfaces of platforms 60A and 60B and substrate 2 remain substantially parallel when substrate 2 contacts the offsets. The benefit of maintaining these two surfaces in parallel is that the volume enclosed between these two surfaces is thus defined and can be precisely controlled. If the two surfaces are not substantially parallel, and the angle between them changes, then the volume between them also changes and is not fixed and precisely controlled. In addition, the fluids may not apply uniformly to the specimen if such two surfaces are not substantially parallel.

As used herein, the phrase "substantially parallel" means that two surfaces are exactly parallel or nearly parallel, so that imperfections in the surface flatness of substrate 2 are reduced or eliminated when substrate 2 contacts the offsets. For example, although great care is taken in the production of substrates, certain substrates may have imperfections such as twist and/or non-coplanar corners. In the systems and methods disclosed herein, the use of offsets assists in correcting these imperfections by improving the surface flatness of substrate 2 where needed, orienting substrate 2 in a substantially parallel relationship to platforms 60A and 60B in the process. The phrase "substantially parallel" covers situations in which the two surfaces are not perfectly flat, but the offsets are all the same size or height, so that at least the contact points of a surface of the substrate with the offsets are in the same plane.

Figure 6A:
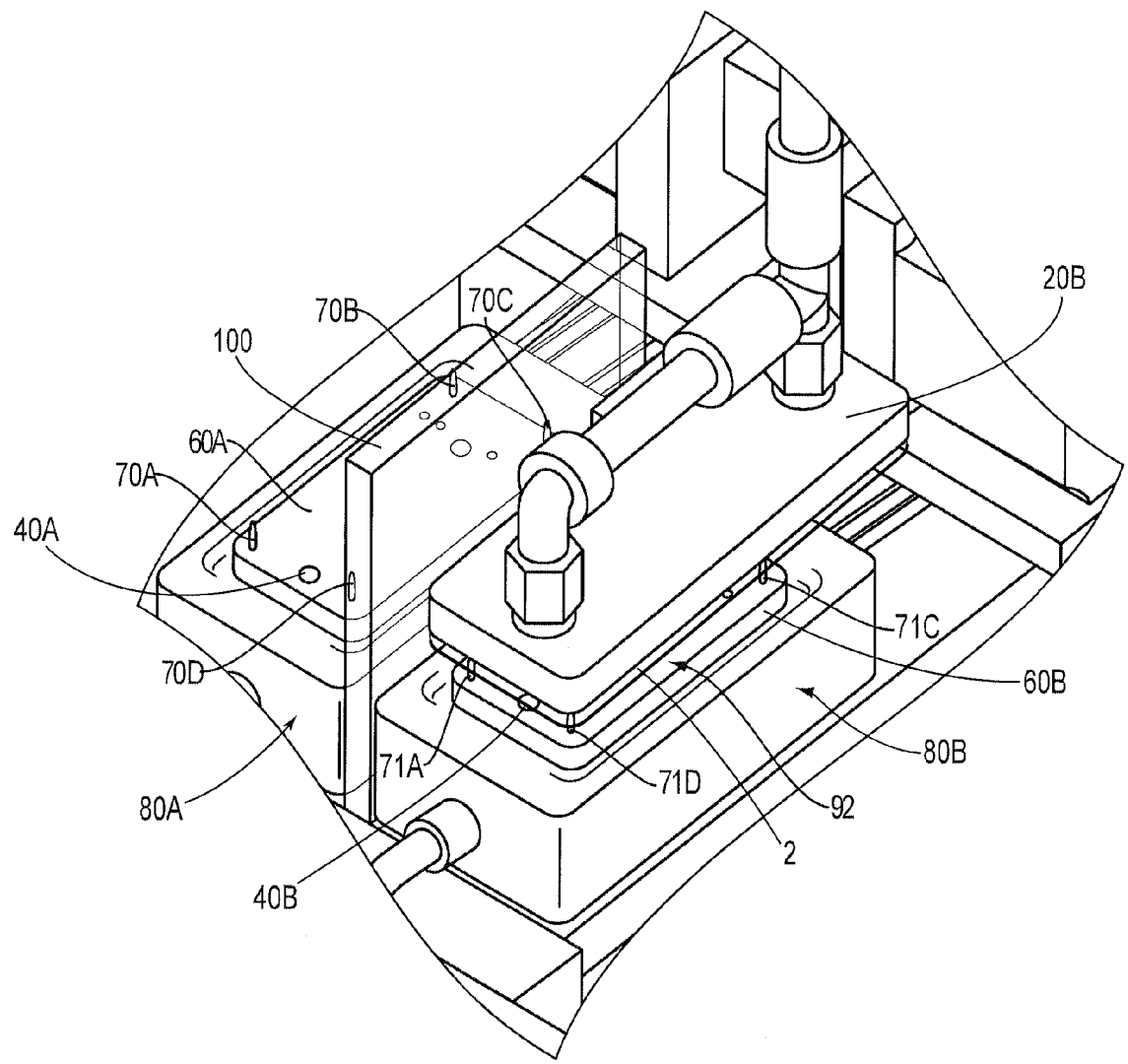
FIG. 6A is an expanded perspective view of a portion of the apparatus of FIG. 1 showing specimen gripper 20B, platform 60B, and block 80B in detail.

FIG. 6A shows substrate 2 with specimen 3 (specimen not shown), substrate gripper 20B, blocks 80A, 80B, platforms 60A, 60B, offsets 70A-70D and 71A-71D, and separation 92 between substrate 2 and platform 60B. Separation 92 allows fluids to travel between the surface of platform 60B containing ports 40B-45B and substrate 2 containing specimen 3. The separation distance required for optimal specimen fixing, staining, and rinsing will vary depending on the flow rate of fluids dispensed from ports 40B-45B (and/or ports 40A-45A), port diameter, the viscosity of the fluids applied during processing, and the amount of suction available for removing fluids from the substrate, separation, and platform.

In some embodiments, for example, offsets providing a separation 92 of about 100-200 microns between the surface of platform 60B and substrate 2 enable fixing, staining, and rinsing for specimens comprising blood cells in embodiments capable of dispensing fluids at flow rates ranging from 70 to 140 microliters per second (e.g., 90, 115, or 125 microliters per second) from ports 40B-45B having a diameter ranging from 500 to 1,500 microns. In general, the size or height of separation 92 can vary from about 50 microns to 1,000 microns for certain embodiments (e.g., from about 50 to 500 microns, from about 75 to 250 microns, from about 100 to 200 microns), provided such embodiments are capable of overcoming surface tension from fluids in the separation while dispensing and removing fluid during specimen processing. In addition, in certain embodiments, the diameters of ports located on platform 60A and/or 60B can vary from about 125 microns to 5,000 microns.

Figure 6B:
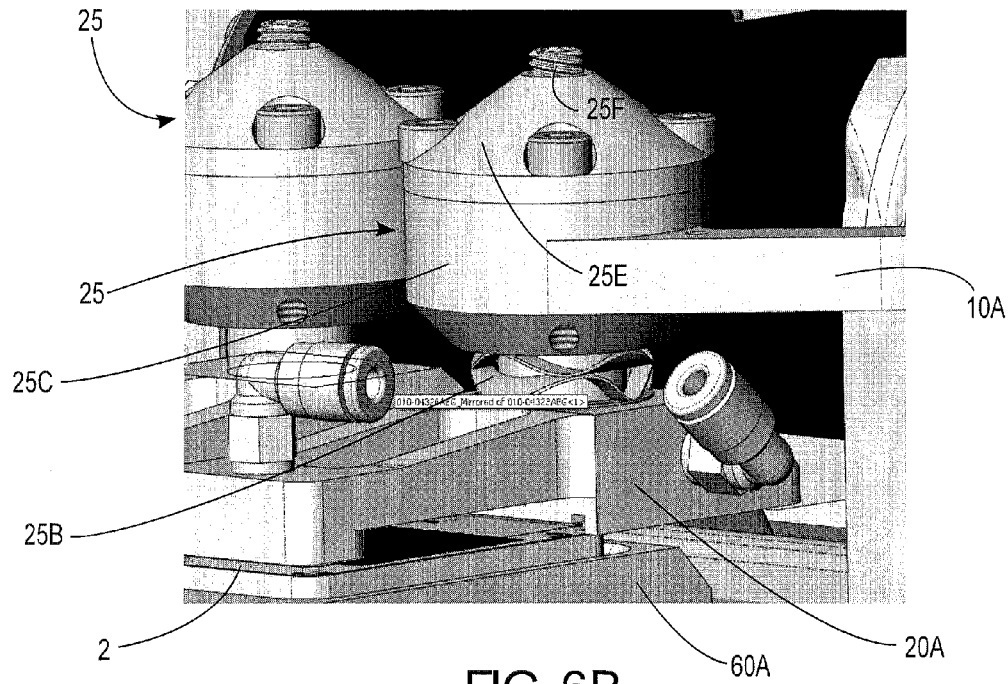
FIG. 6B is a perspective view of a ball joint mechanism of the apparatus of FIG. 1.
Figure 6C:
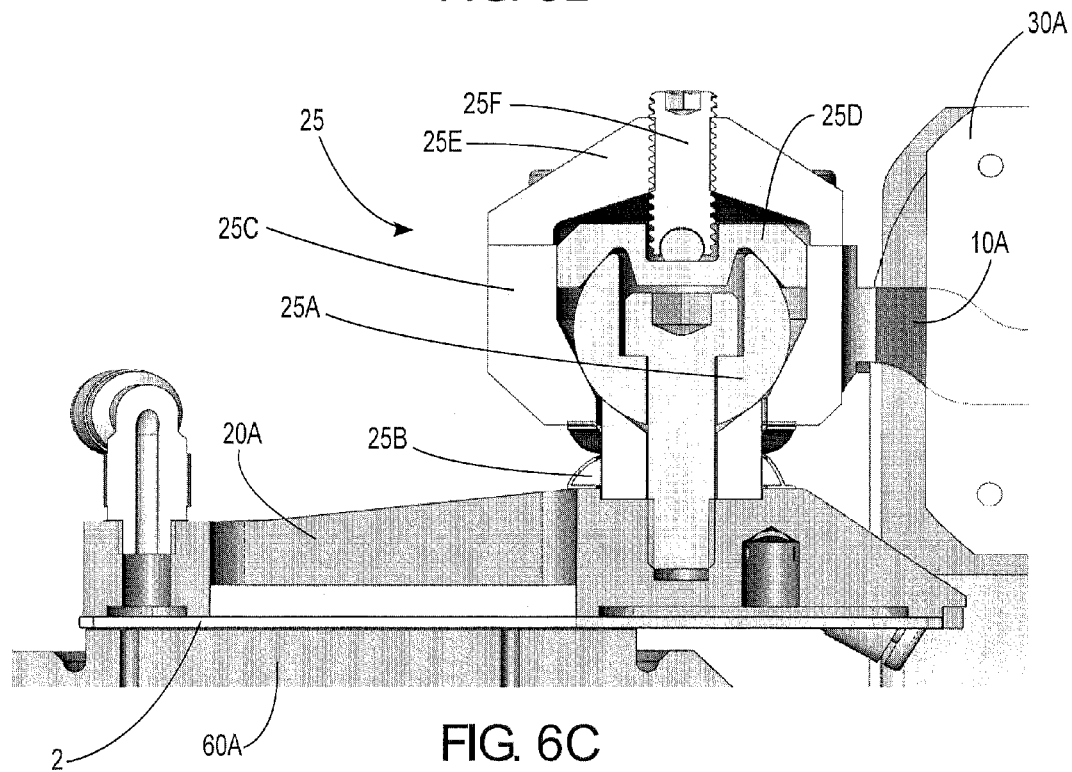
FIG. 6C is a cross-sectional view of the ball joint mechanism of FIG. 6B.

FIGS. 6B and 6C show a ball joint mechanism 25 that can be used to align a substrate gripper 20A to be parallel with a platform 60A. The ball joint mechanism 25 can include a ball member 25A that is rigidly fixed to the substrate gripper 20A, a deflection element 25B (e.g., a spring), a lower socket 25C that is rigidly connected to the substrate arm 10A, an upper socket 25D, a cap 25E that is fixed to the lower socket 25C (e.g., using fasteners), and a set screw 25F. In some embodiments, during manufacturing and/or set up of the machine 1 and substrate grippers 20A and/or 20B, the ball joint mechanism 25 can be adjusted to compensate for any misalignment that may be present due to tolerance stack-up or fabrication problems. To adjust the ball joint mechanism 25, in some embodiments, the set screw 25F is loosened and the substrate arm 10A is moved to the closed position. Since the set screw 25F is loosened, the substrate gripper 20A, while gripping a substrate 2, is able to lay substantially parallel to the platform 60A while the substrate 2 positioned along the contact offsets 70. Alternatively, in some embodiments, the number of offsets on platform 60 can be reduced or eliminated completely; a shim with a thickness corresponding to the desired separation distance can be used temporarily during set up or calibration of machine 1 in conjunction with ball joint mechanism 25 to set separation 92 at a desired distance for specimen processing. Although the ball joint mechanism 25 is loosened, the deflection element 25B applies a force to keep the substrate gripper 20A semi-fixed to the substrate arm 10A so that it is able to move independently, but it is not so loose and not free to move so much as to interfere with, or cause damage to, other components of the machine 1. Once the substrate 2 is pressed firm in a closed position so the substrate 2 is substantially parallel to the platform 60A, the set screw 25F can be tightened to secure the ball joint mechanism 25. As shown, when tightened, the set screw 25F applies a downward force on the upper socket 25D and thus applies a frictional force to the top of the ball member 25A via the upper socket 25D. Since the lower socket 25C is fixed to the cap 25E, the force created by the set screw 25F also lifts the lower socket 25C such that the lower socket 25C applies a frictional force to the bottom side of the ball member 25A to constrain the ball member 25A within the upper and lower sockets 25C, 25D. Once constrained to the ball member 25A, the substrate gripper 20A becomes fixed to the substrate arm 10A.

Typically, once the substrate gripper 20A is positioned and constrained with the set screw 25F, the ball joint mechanism 25 need not be adjusted again during normal use. However, if the substrate gripper 20A becomes misaligned and therefore the ball joint mechanism 25 requires adjustment (e.g., due to damage, machine repair, poor performance, or other reasons), the set screw 25F can be loosened, the substrate gripper 20A can be moved to a closed position to position so that a substrate gripped by the substrate gripper 20A is substantially parallel to the platform 60A, and then set screw 25F can be tightened to secure the ball joint mechanism 25.

In general, actuators 30A and/or 30B can be configured to adjust the position of substrate arms 10A and/or 10B to vary the extent of separation between the surface of platforms 60A and/or 60B and substrate 2. Varying this separation provides greater flexibility in embodiments that allow for adjusting the fluids assigned to each port, flow rates, fluid viscosities, and evacuation forces from platforms 60A and/or 60B. For example, a 100 micron separation 92 can provide sufficient specimen fixing, staining, and rinsing when fluids applied from platform 60A are dispensed at a flow rate of 70 microliters per second from ports 40A-45A having port diameters ranging from 500 microns to 1,500 microns. Alternatively, with a separation 92 distance between the surface of platform 60A and substrate 2 of approximately 200 microns, a higher flow rate for fluids dispensed from ports 40A-45A, such as 115-140 microliters per second, can be used for specimen processing.

As disclosed above, machine 1 may contain a series of ports and tubes for dispersing and removing fluids applied during specimen processing. The following discussion describes various ports, tubes, and other components associated with platform 60A, but similar considerations apply to platform 60B and its associated components. FIG. 2 shows a close up view of the apparatus shown in FIG. 1, and shows in detail ports 40A-45A on platform 60A and tubes 50A-55A connected to block 80A. Tubes 52A-55A distribute certain fluids including one or more fixatives, stains, and rinse solutions across the platform, into the separation, and onto the substrate.

Referring to FIG. 2, the top side of platform 60A includes six ports 40A-45A that are connected to tubes 50A-55A. Fluids are driven by one or more pumps through the tubes and ports onto substrate 2. One or more fluid reservoirs 210A-213A (such as a first stain reservoir 211A, a second stain reservoir 212A, a fixative reservoir 210A, and a rinse solution reservoir 213A), e.g., as shown in FIG. 4, can direct fluid onto platform 60A and substrate 2. The diameters of ports 40A-45A shown in FIGS. 1-3 range from approximately 500 microns to 1,500 microns, although the diameters can also be smaller or larger in certain embodiments. In some embodiments, the diameters of the vacuum ports 40A and 41A are more than twice the diameters of fluid ports 42A-45A.

Each of ports 40A-45A is typically dedicated to a particular fluid or vacuum source. Alternatively, more than one port may be used for each fluid or vacuum source, or multiple tubes from various fluid and vacuum sources may connect to a single port located on platform 60A. For example, in some embodiments, only one port on platform 60A may be used for waste removal, but when using more viscous fluids, the single port may not provide sufficient suction to evacuate residual fluid from the platform. Thus, it may be desirable in certain embodiments to provide two suction ports at different positions on the platform (e.g., one suction port at each end of the platform) for removing excess stain, fixative, and rinse fluids as shown with ports 40A and 41A in FIG. 2. Further highlighting the variability of fluid-to-port configurations, in certain embodiments, a single port on platform 60A may be dedicated for a particular stain, while in other embodiments multiple ports are used for applying stains during specimen processing. Indeed, various combinations relating to the number of ports, port locations, and fluids assigned to each port and fluid tube may be used in different embodiments of the invention.

Ports 40A-45A can generally be positioned as desired on platform 60A to provide for fluid delivery to, and fluid removal from, substrate 2. Typically, each of the fluid ports is positioned on platform 60A such that the port's aperture is not positioned directly adjacent or beneath specimen 3 on substrate 2 when the specimen is undergoing processing. With certain combinations of specimens and stains, for example, if stains are dispensed from a port located directly adjacent or beneath a portion of specimen 3, a larger quantity of stain may be applied to cells in that portion (in the vicinity of the port) than to cells in other portions of the specimen. As a result, cells receiving the larger quantity of stain may appear darker in specimen images, and this non-uniform staining of specimen cells can complicate manual and automated evaluation of the specimen and introduce errors into diagnostic measurements and analytical outcomes based on the images. Thus, fluid ports that deliver stain to specimen 3 can be spaced a certain distance from the specimen-containing area of a slide to improve staining results.

In addition, the use of pairs of ports, e.g., multiple pairs of ports, located opposite each other, can also improve staining uniformity. For example, in some embodiments, two ports are used to deliver stain to specimen 3. The two ports can be located on platform 60A at positions spaced a certain distance (e.g., are offset) from the edges of specimen 3, and located opposite each other in a direction parallel to the short edges of platform 60A. When stain is dispensed from the two spaced ports, a relatively uniform quantity of stain is deposited on the cells in different regions of specimen 3, and improved staining homogeneity is observed in specimen images.

Similarly, while ports 40A-45A can generally be positioned as desired to remove excess fluids from the surface of substrate 2 using one or more vacuum sources, in some embodiments ports that are used for fluid removal are spaced at a distance from positions on platform 60A that are directly beneath cells within specimen 3 on substrate 2. Positioning waste removal ports in this manner (i.e., not directly opposing a portion of specimen 3) reduces the chances that when such ports are actuated to evacuate fluids from substrate 2, cells from specimen 3 are inadvertently damaged or drawn into the fluid removal ports. In certain embodiments, due to the difference in lengths of the long and short sides of platform 60A, the waste removal ports are spaced apart from the edge of the specimen area and arranged opposite each other along a direction parallel to the long edges of platform 60A.

Fixative Phases

Fluid tubes 52A-55A and 52B-55B can be positioned to deliver fixative to platforms 60A and 60B, separation 92, substrate 2, and specimen 3 during specimen processing. Fixatives that can be used include chemicals used for protecting biological samples from decay, and such fixatives can impede biochemical reactions occurring in the specimen and increase the mechanical strength and stability of the specimen. Various fixatives can be used including, but not limited to, methanol, ethanol, isopropanol, acetone, formaldehyde, glutaraldehyde, EDTA, surfactants, metal salts, metal ions, urea, and amino compounds.

Referring to FIG. 4, one or more fluid tubes 52-55A can be connected to a port inside platform 60A and a respective fixative reservoir 210A. The fluid tubes may also include a connection to a pump 200A and/or a valve capable of directing fixatives from the reservoir through the tube and a port located on the platform, and onto a substrate and specimen. As an example, pump 200A can direct fixative from reservoir 210A through tube 54A, through block 80A, out from port 44A, onto platform 60A, into the separation 92 between the platform 60A and substrate 2, and onto substrate 2 containing specimen 3. After applying a specific quantity of fixative to substrate 2, a vacuum or other suction source 220A and/or 221A can evacuate residual fixative from platform 60A, the separation 92, and substrate 2 into waste container 230A and/or 231A via one or more of ports 40A and/or 41A through waste tubes 50A and 51A.

Figure 9:
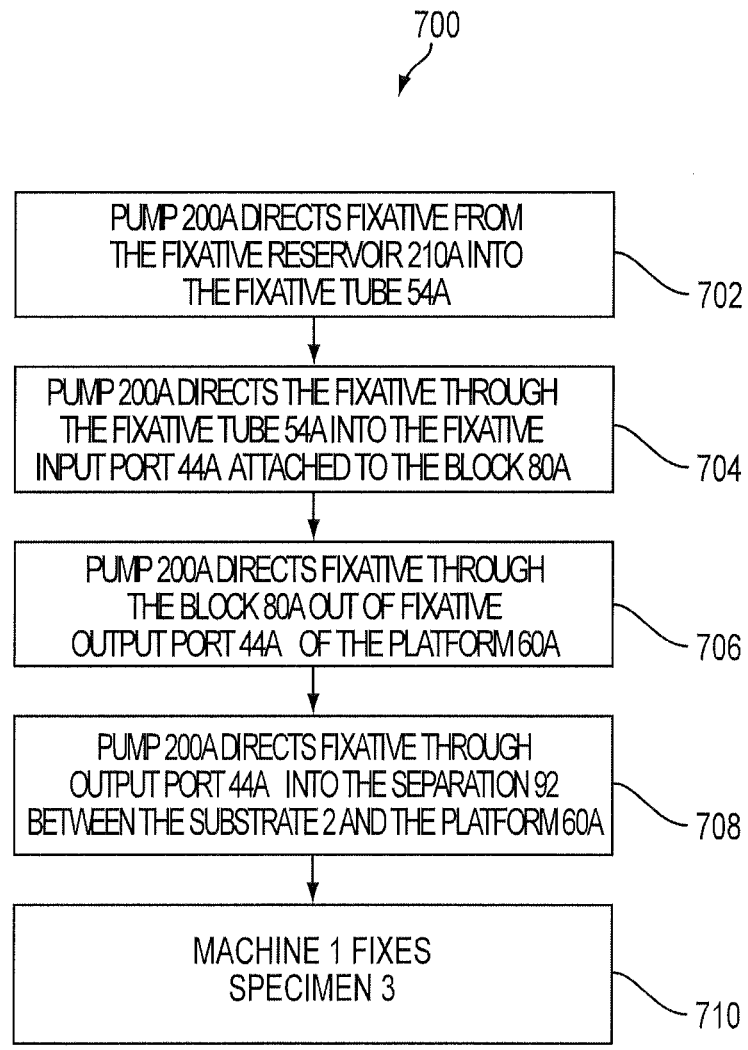
FIG. 9 is a flow chart showing a series of steps for applying fixative to a specimen.

FIG. 9 shows a flow chart 700 that includes a series of steps for applying fixative to a specimen. In step 702, a pump (e.g., pump 200A) directs fixative (e.g., methanol) from a reservoir (e.g., reservoir 210A) into a fixative tube (e.g., tube 54A). In step 704, the fixative is directed into port 44A attached to block 80A. Then, in step 706, the fixative is directed out of port 44A in platform 60A. In step 708, the fixative is directed out through port 44A and into separation 92 between substrate 2 and platform 60A. Finally, in step 710, specimen 3 on substrate 2 is fixed by the fixative solution.

In some embodiments, pump 200A directs methanol through tube 54A and port 44A, onto platform 60A and into the separation 92 at a flow rate of 70 microliters per second for a period of four seconds. A vacuum or other suction source 220A and/or 221A then removes residual methanol present in separation 92 and/or on the platform 60A and substrate 2 using ports 40A and/or 41A and waste tubes 50A and/or 51A (further described below). Next, the pump 200A can again direct methanol through tube 54A and port 44A, and onto platform 60A at a flow rate of 70 microliters per second for a period of four seconds, followed by a second fluid evacuation process. This process of fixing and evacuating can be repeated again, using the same or a different fixative, depending on the type of biological specimen requiring fixation. Further, machine 1 is capable of varying the frequency and flow rates for each fixing phase. Other flow rates sufficient to overcome any surface tension in the fluid located in separation 92 and fix specimen 3 for further processing and evaluation can also be used. By adjusting the frequency and/or flow rate of the fixing phases, machine 1 can achieve optimal fixation for various specimens using several different fixatives. Machine instructions for different types of specimens can be hardwired or preprogrammed in control unit 5 and selected by a system operator as needed.

In general, a wide variety of fixatives can be applied to specimens during fixative phases. For example, 85% methanol can be used as the fixative. For some stains, an ethyl alcohol or formaldehyde based fixative can be used. Additional fixative formulations that can be used to prepare the specimen are disclosed, for example, in U.S. Provisional Patent Application No. 61/505,011, the entire contents of which are incorporated by reference herein.

Staining Phases

Machine 1 also includes tubes and ports configured to apply one or more dyes or stains to a specimen fixed to a substrate in one or more staining phases. Staining a specimen increases the contrast of the specimen when it is viewed or imaged under a microscope or other imaging device. Romanowsky stains and/or other dyes or stains can be used, including hematoxylin and eosin, fluorescein, thiazin stains using antibodies, nucleic acid probes, and/or metal salts and ions. Additional stain formulations that can be used to prepare the specimen are disclosed, for example, in U.S. Provisional Patent Application No. 61/505,011.

Figure 10:
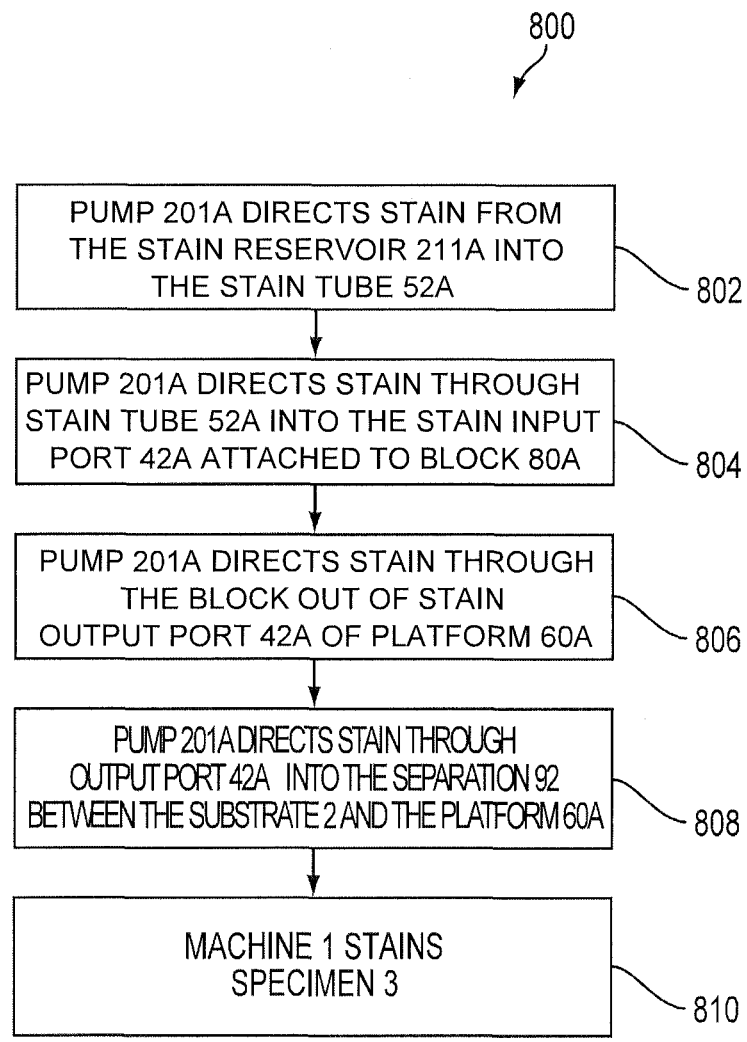
FIG. 10 is a flow chart showing a series of steps for applying stain to a specimen.

FIG. 10 is a flow chart 800 that includes a series of steps for applying stain to a specimen. In step 802, a pump (e.g., pump 201A) directs dye or stain from a reservoir (e.g., reservoir 211A) into a stain tube (e.g., tube 52A). In step 804, the stain is directed into a port (e.g., port 42A) attached to block 80A. Next, in step 806, the stain flows out of port 42A in platform 60A. In step 808, the stain flows into separation 92 between substrate 2 and platform 60A and thereafter, in step 810, stains specimen 3 on substrate 2.

In some embodiments, multiple tubes and ports can be used to apply stain to specimen 3. For example, a second pump (e.g., pump 202A) can direct stain (e.g., the same stain or a different stain from that dispensed from reservoir 211A) from reservoir 212A through tube 53A and port 43A and onto platform 60A. In certain embodiments, two or more fluid tubes may connect to a shared stain reservoir or pump and/or valve used to direct stain through the ports and onto the platform. Referring back to FIG. 2, tube 52A may deliver red stain, such as a fluorescein dye, to the platform, substrate 3, and specimen 2. Tube 53A may deliver blue stain, such as a thiazin dye. In FIGS. 1-6, the numbers, locations, and sizes of the ports on platform 60A are selected to optimize the application of stain to a specimen fixed to the substrate. If other stains are selected, a different number, locations, and sizes of ports may be preferable depending on the viscosity of the stain.

Each of ports 40A-45A (and 40B-45B) can include both an input channel for receiving fluid and an output channel for outputting fluid. In some embodiments, the output channels of the rinse 45A, fixative 44A, and staining ports 42A-43A are on the upper surface of platform 60A, and the input channels of vacuum ports 40A and 41A may be on opposite ends of the upper surface of platform 60A. The input channels of the rinse 45A, fixative 44A, and staining ports 42A-43A may be situated on the same lateral side of block 80A, and the output channels of the vacuum ports 40A and 41A can be positioned on opposite lateral sides of block 80A.

By way of example and with reference to FIGS. 2 and 10, control system 5 instructs a pump (e.g., pump 201A) in step 802 to direct a stain (e.g., a stain comprising fluorescein dye) from a stain reservoir into fluid tube 52A. In step 804, the stain enters port 42A from the fluid tube. Then, in step 806, the stain leaves port 42A at a flow rate of 140 microliters per second, for a five second period, and in step 808, the stain is deposited into separation 92 between platform 60A and substrate 2 containing specimen 3. In step 810, specimen 3 on substrate 2 is stained. Following staining, a vacuum or other suction source (e.g., pumps 220 and/or 221) may then evacuate residual stain present in separation 92, on platform 60A, and on substrate 3 using ports 40A-41A and waste tubes 50A-51A.

Machine 1 can be programmed to repeat these staining and evacuation phases after a delay (e.g., a delay of between 3 seconds and 10 seconds, such as a five second delay), following the first staining phase. A second pump 202A can be instructed by control system 5 to direct thiazin dye from a stain reservoir through fluid tube 53A, out port 43A at a flow rate of 140 microliters per second, and onto platform 60A for a period of time, e.g., three seconds. A vacuum or other suction source (e.g., pump 220A and/or 221) may then evacuate residual thiazin dye present in separation 92 and/or on platform 60A and/or on substrate 2 using ports 40A-41A and waste tubes 50A-51A. As with the fixing phases, machine 1 is capable of varying the frequency, delay times, and flow rates for each staining phase. The flow rate may range, e.g., from 70 to 140 microliters per second, or may be smaller or greater than the outer limits of this range (e.g., 10 to 500 microliters per second) provided the flow rate is sufficient to overcome any surface tension present in the fluid located in separation 92 and desirably stain the specimen for the intended evaluation.

Exemplary stains that can be applied to specimens include, but are not limited to: Wright-Giemsa stain, Giemsa stains, and Romanowsky stains. Other agents such immunocytochemical reagents or other markers of specific cell components can also be applied to specimens.

Waste Fluid Removal

As referenced above, a vacuum or other suction source 220 and/or 221 can evacuate residual fluid from substrate 2, separation 92, and platform 60A during or between fixing and staining phases. Referring to FIG. 1, one or more waste tubes can be connected to sides 82A and 84A of block 80A. Waste or vacuum tubes 50A and 51A are used to withdraw fluid and small particulate matter from platform 60A, separation 92, and substrate 2 into a waste container or other location separate from machine 1. With reference to FIG. 2, waste tubes 51A and 51B may be connected to separate vacuum sources 220 and 221, and waste containers 230 and 231, at the distal ends of the waste tubes. Alternatively, two or more waste tubes can be connected to a single vacuum source, and the same waste container, as shown in FIG. 4. Waste tubes 50A and 50B may extend through pinch valves 90A and 90B, respectively.

A vacuum or other source (e.g., vacuum pump 220 and/or 221) for applying suction may be connected to one or more of waste tubes 50A, 50B, 51A, and 51B to draw fluid from the platforms 60A and/or 60B, separation 92, and substrate 2 into waste containers 230 and 231. The vacuum force applied within the waste tubes may be equivalent to negative one to negative ten pounds per square inch ("psi") to provide sufficient suction for removing fluids when the separation between the substrate 2 and the platform is between 100 to 200 microns. In general, as used herein, "negative" pressure refers to a pressure less than the ambient pressure within machine 1 or the environment surrounding machine 1. For example, in some embodiments, the environment surrounding machine 1 has an ambient air pressure of approximately one atmosphere. "Negative" pressures refer to pressures that are less than this ambient air pressure (e.g., a pressure of negative one psi applied to a fluid is a pressure of one psi less than the ambient air pressure exerted on the fluid). Other vacuums ranging from negative 0.1 psi to negative 14 psi (e.g., negative six psi), or greater, can be used provided such vacuums are sufficient to overcome any surface tension in the fluid present in the separation and remove all residual fluid in the separation and on the substrate and specimen. In addition, immediately prior to applying vacuum to evacuate fluids from the separation, actuator 30A can raise the proximate edge of substrate 2 a distance of 15-35 microns from the specimen processing position. This increased separation between substrate 2 and platform 60 can improve evacuation of any residual fluids in separation 92 during a vacuum phase.

Figure 11A:
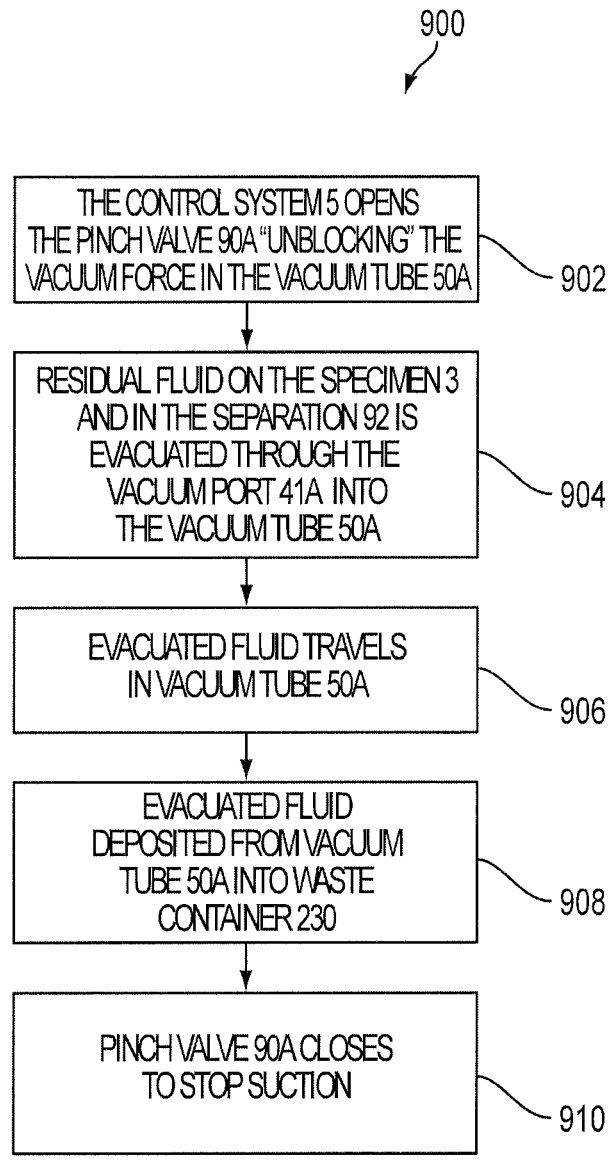
FIG. 11A is a flow chart showing a series of steps for removing excess fluid from a substrate.

In some embodiments, control system 5 is configured to vary the frequency and vacuum applied for fluid removal during specimen processing. FIG. 11A includes a flow chart 900 that features a series of steps for removing excess fluid from a substrate. Following a fixing phase, for example, control system 5 can open pinch valves 90A and/or 90C in step 902 and apply a vacuum of negative 5 psi in the waste tubes (e.g., waste tubes 50A and 51A) for a five second period. During this period, fixative is removed (step 904) the separation, substrate, and platform through ports 40A and 41A. The fluid travels through the waste tubes in step 906, and is deposited in into one or more waste containers (e.g., containers 230 and/or 231) in step 908. Once the evacuation period expires, control system 5 can instruct one or more of the pinch valves 90A, 90C to close off the waste tubes 50A and/or 51A in step 910, thereby preventing further evacuation by the vacuum 220-221. Control system 5 may direct machine 1 to repeat this fluid removal step after each fixing phase.

Figure 11B:
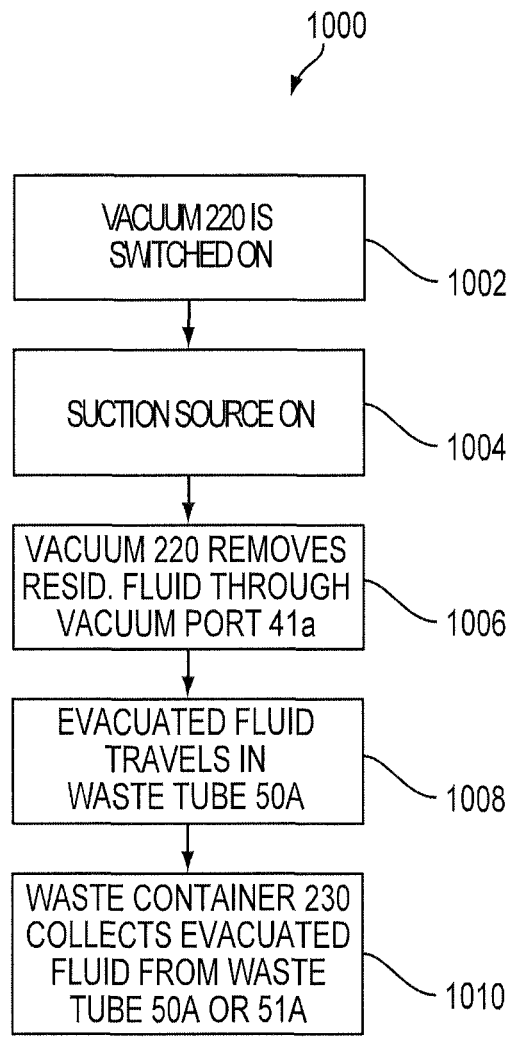
FIG. 11B is a flow chart showing an alternate series of steps for removing excess fluid from a substrate.

FIG. 11B includes a flow chart 1000 that features an alternate series of steps for removing excess fluid from a substrate. The method in flow chart 1000 does not use pinch valves to seal waste tubes. Instead, after a fluid application phase, suction source 220 and/or 221 are initialized in step 1002 and enter an active state in step 1004. The suction source applies a vacuum of negative 3 psi in waste tubes 50A and/or 51A for a four second period to remove fluid from separation 92, substrate 2, and platform 60A through ports 40A and 41A in step 1006. The evacuated fluid travels through waste tubes 50A and/or 51A in step 1008, and is deposited in one or more waste containers 230, 231 in step 1010. Machine 1 may repeat this fluid removal step after each fluid application phase. By varying the frequency and pressure applied during fluid removal steps, machine 1 may achieve optimal fixing, staining, and rinsing of biological specimens.

Pinch values 90A, 90B, 90C, and 90D close off waste tubes 50A, 50B, 51A, and 51B, as shown in FIG. 1. The pinch valves 90A-90D may be mechanically, electrically, hydraulically, or pneumatically actuated through actuators contained within or external to the valves. Pinch valves 90A-90D operate to prohibit fluid flow through waste tubes 50A, 50B, 51A, and 51B. For example, when changing or emptying a full waste container 230 from machine 1, it may be desirable to close the pinch valves (90A-90D) to prevent leakage of residual fluids present in the waste tubes. Different valve types or other mechanisms such as clamps or stoppers may be used with embodiments of machine 1 to close the waste tubes 50A, 50B, 51A, and 51B.

Rinsing Phases

Rinse solutions can be applied during specimen processing with machine 1 in one or more rinse phases. For example, it may be desirable to remove residual and/or excess fluids from specimen 3 on substrate 2, separation 92, and platforms 60A and/or 60B between fixing phases, between staining phases, and/or between fixing and staining phases. Rinse solutions compatible with the present systems and methods include distilled water; buffered, aqueous solutions; organic solvents; and mixtures of aqueous and organic solvents, with or without buffering. Additional formulations for rinse solutions that can be used to prepare the specimen are disclosed, for example, in U.S. Provisional Patent Application No. 61/505,011.

Figure 12:
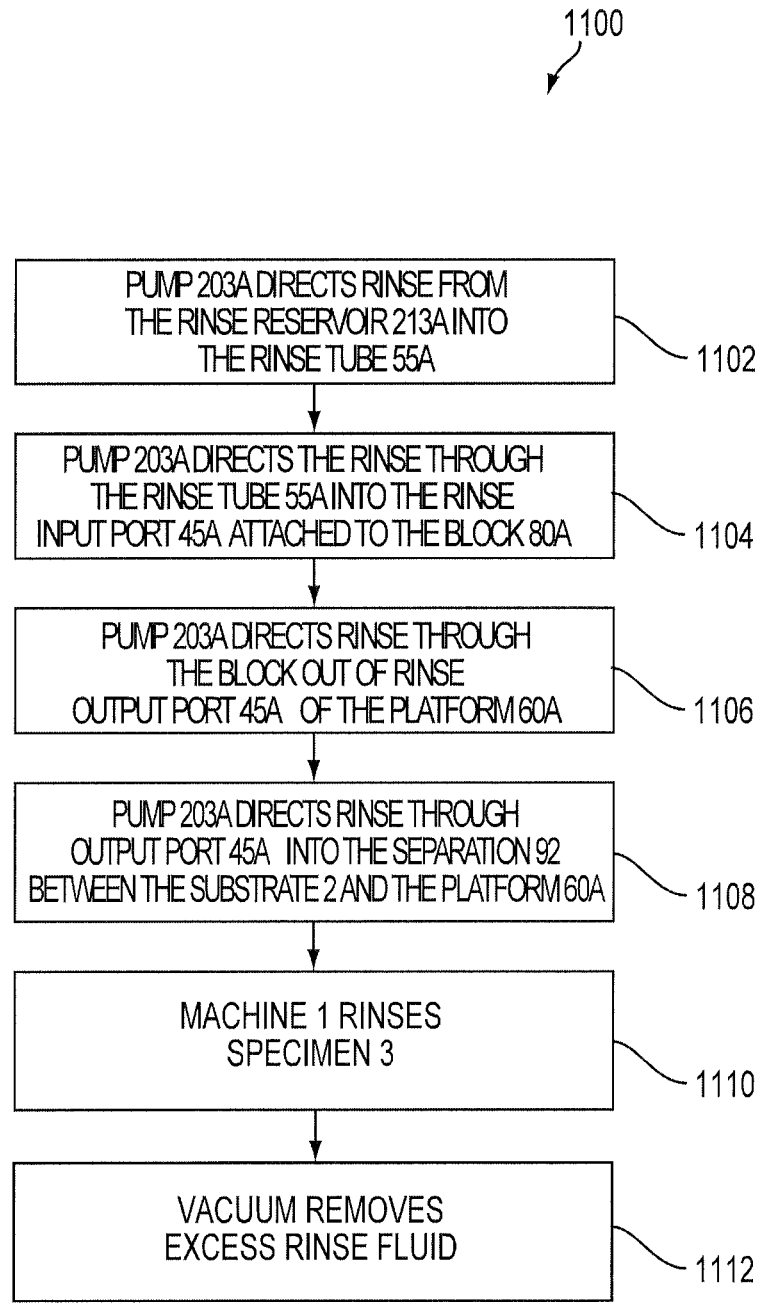
FIG. 12 is a flow chart showing a series of steps for rinsing a specimen.

FIG. 12 includes a flow chart 1100 featuring a series of steps for rinsing a specimen. In step 1102, a pump (e.g., pump 203A) directs rinse solution (e.g., comprising distilled water) from a reservoir (e.g., reservoir 213A) into a rinse tube (e.g., rinse tube 55A). In step 1104, the rinse solution enters port 45A connected to block 80A. In step 1106, the rinse solution flows onto platform 60A through the output channel of port 45A, and in step 1108, the rinse solution enters separation 92 between substrate 2 and platform 60A. In step 1110, rinsing of specimen 3 is performed. Finally, in step 1112, a vacuum source 220, 221 applies suction to one or more of waste tubes 50A and 51A to remove rinse solution from separation 92 and substrate 2; the rinse solution is transported to waste container 230 and/or 231.

In some embodiments, control system 5 may direct pump 203A to apply the rinse solution at a flow rate of, e.g., 70 microliters per second for a period of, e.g., five seconds. As with fixing phases, control system 5 may vary the duration and flow rate of each rinse phase and the number of rinse phases. In addition, control system 5 may adjust the placement of one or more rinse phases during specimen processing. Control system 5 may, for example, direct that a rinse phase occur once, after completion of all fixing phases, and that a second rinse phase occur once, after completion of all staining phases. Alternatively, rinse phases may be interspersed between two or more fixing phases or between two or more staining phases.

Agitation Phases

Figure 13:
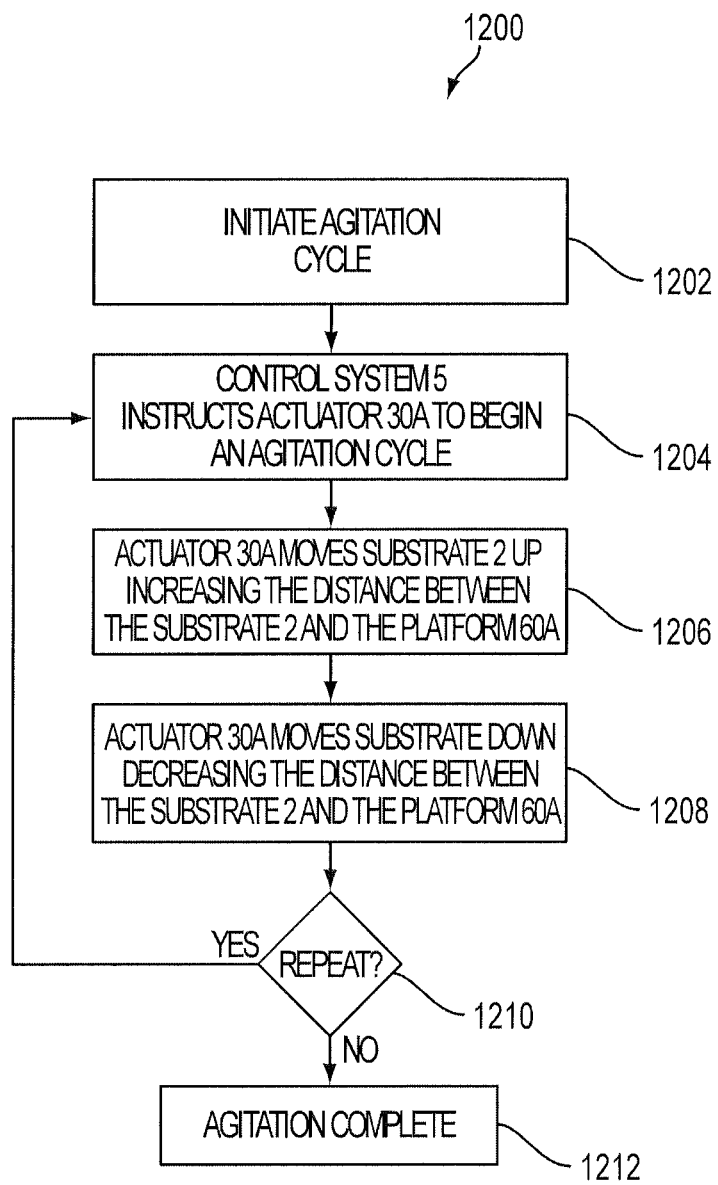
FIG. 13 is a flow chart showing a series of steps for agitating a specimen.

Specimen processing in certain embodiments may include one or more agitation phases to disperse fixative, stain, and/or rinse fluids throughout separation 92, substrate 2 containing specimen 3, and platforms 60A and/or 60B during the fixing, staining, and/or rinsing phases. FIG. 13 includes flow chart 1200 that features a series of steps for agitating a specimen. Actuator 30A and/or 30B, shown in FIG. 3A, can provide fine movement adjustment for changing the position of substrate 2 relative to platform 60A and/or 60B.

Control system 5 can include software and/or hardware for instructing the actuator 30A and/or 30B to initiate an agitation phase. Actuator 30A and/or 30B can be configured to move substrate arm 20A and/or 20B up and down upon an agitation initiation command from the control system. The agitation phase may repeat for a predetermined number of agitation cycles. The term "agitation cycle," as used herein, refers to motion from a starting position in an upward direction, followed by movement in a downward direction opposite to the upward direction. In some embodiments, one or more agitation cycles return substrate 2 to the starting position at the conclusion of each cycle, or at least at the conclusion of some cycles. In certain embodiments, substrate 2 does not return to the starting position at the conclusion of some or all of the agitation cycles, but each cycle still includes an upward motion followed by a downward motion. Actuator 30A and/or 30B typically continues moving substrate 2 in one or more agitation cycles until a stop command is sent to the actuator from the control system 5. An agitation phase may temporarily increase the separation size (separation distance) between substrate 2 and the surface of platform 60A and/or 60B, and then return the substrate to the specimen processing position. In addition, an agitation phase may include a series of movements that shift substrate 2 between an angular position relative to the surface of platform 60A and/or 60B and the specimen processing position. Surface tension in the fluids dispensed into the separation between the platform and substrate 2 causes a redistribution of fluid molecules on the substrate when the substrate moves from the specimen processing position during the agitation phase and can advantageously improve fluid distribution across the specimen.

Other methods can also be used to move substrate 2 relative to the platforms during agitation phases. For example, in some embodiments, the positions of one or more of offsets 70A-D and/or 71A-D (e.g., the amount by which the offsets extend above the surfaces of platforms 60A and/or 60B) can be rapidly adjusted to agitate specimen 3. In certain embodiments, the positions of platforms 60A and/or 60B can be adjusted to cause agitation of specimen 3. For example, platforms 60A and/or 60B can be moved alternately up and down (e.g., corresponding to the direction of movement of substrate 2 described above) to cause agitation of specimen 3.

In some embodiments, agitation of specimen 3 can be effected by varying the extent to which actuator 30A and/or 30B drives substrate 2 towards offsets 70A-D and/or 71A-D when the substrate arms are made of a material that flexes, as discussed below. Strain gauges can be used to measure and adjust the frequency of the agitation applied to substrate 2 by detecting the variation in strain in the substrate arms as a function of time.

Referring to FIG. 13, in a first step 1202, an agitation phase is initiated. In step 1204, control system 5 instructs actuator 30A to begin an agitation cycle. In response to this instruction, actuator 30A rotates substrate 2 upward in step 1206, increasing the distance between substrate 2 and platform 60A. Then, in step 1208, actuator 30A rotates substrate 2 downward toward platform 60A, reducing the distance between the substrate and platform 60A. In decision step 1210, if the agitation phase is to continue, control returns to step 1204 and the rotation of substrate 2 by actuator 30A occurs again in another agitation cycle. If the agitation phase is to terminate, then control passes from step 1210 to step 1212, where substrate 2 is returned to its initial position with agitation complete.

The agitation phase can include one or more agitation cycles applied through actuator 30A and/or 30B. Further, agitation phases can occur once or multiple times during each of the fixative, stain, and/or rinse phases and in varying frequencies between each of the fixing, staining, and/or rinsing phases. For example, and referring to FIG. 3A, actuator 30A and/or 30B may raise the proximate edge of substrate 2 vertically a distance of 35 microns from the specimen processing position and subsequently return substrate 2 to the specimen processing position three times, once after each fixing, staining, and rinse phase. Actuator 30A and/or 30B may complete each agitation cycle in two seconds (e.g., one second to raise the proximate edge of substrate 2 vertically a distance of 35 microns from the specimen processing position and one second to return the substrate to the specimen processing position). Machine 1 is capable of carrying out instructions to vary the agitation frequency and distance for each agitation cycle and/or phase. For example, an agitation phase may include actuator 30A and/or 30B raising the proximate edge of substrate 2 vertically a distance of 5 microns from the specimen processing position and then returning the substrate to the specimen processing position, 10 to 20 times per second.

Alternative combinations of agitation distances and frequencies can also be used. For example, in some embodiments, the agitation distance is 5 microns or more (e.g., 15 microns or more, 25 microns or more, 50 microns or more, 100 microns or more, 150 microns or more, 200 microns or more, 250 microns or more, 300 microns or more, 500 microns or more, 700 microns or more, 1 mm or more. For example, in certain embodiments, the agitation distance is between 35 microns and 350 microns.

In some embodiments, the agitation cycle frequency is one cycle per second or more (e.g., two cycles per second or more, three cycles per second or more, four cycles per second or more, five cycles per second or more, seven cycles per second or more, ten cycles per second or more).

Additional agitation techniques can also be used. For example, in some embodiments, substrate gripper 20A and/or 20B may include an actuator that rotates the substrate about an axis perpendicular to the rotational axis of actuator 30A and/or 30B depicted in FIGS. 1 and 3.

Alternatively, platform 60A and/or 60B may be equipped with an offset adjuster for raising or lowering the one or more offsets 70A-D and/or 71A-D during fixing, staining, and rinsing phases. To implement the offset adjuster, platform 60A and/or 60B can include offsets that are attached to an internal plate in the platform. The height of the plate may be varied using an internal actuator, thus varying the height of the offsets. Alternatively, the position of the offsets 70A-D and 71A-D relative to substrate 2 can be changed by instructing the actuator to move platform 60A and/or 60B, or block 80A and/or 80B, thereby changing the separation distance during the agitation phase. Control system 5 can adjust the frequency of fluid cycles, flow rate, offset height, separation distance, and agitation parameters and frequency to process specimens more efficiently, using significantly less fluid volumes during the specimen preparation process as compared to conventional staining and preparing techniques.

In some embodiments, substrate arms may be made of a material that flexes such that if a substrate in the specimen processing position rests against only two offsets extending from the platform, an actuator or other motive force element may rotate the slide further towards the platform surface until the slide rests against all four offsets. Varying the position of the substrate between these two positions may accomplish sufficient agitation during specimen processing. Substrate arms may include strain gauges to monitor the strain in the substrate arm, and may be used to inform control system 5 of the position of the substrate relative to the platform offsets. In addition, the control system may include information corresponding to the thickness imperfections of the substrate, which the control systems may account for when placing the substrate in the specimen processing position or during agitation phases.

Drying Phases

Figure 14:
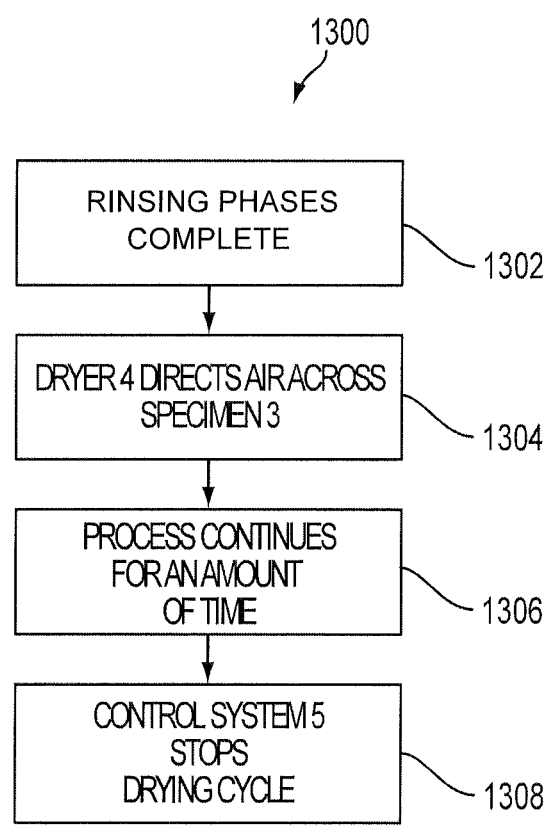
FIG. 14 is a flow chart showing a series of steps for drying a specimen.

In certain embodiments, the control system 5 can dry the specimen using a dryer 4 attached to machine 1. FIG. 14 includes a flow chart 1300 that features a series of steps for drying a specimen. Following the initial step 1302 in which the completion of the staining and other phases (e.g., one or more rinsing phases) is verified, in step 1304 the dryer 4 directs a flow of air across the specimen. The drying process continues in step 1306, until a signal is received from the control unit to stop the drying. When the signal is received, the dryer stops the flow of air across the specimen and the drying phase terminates at step 1308.

In general, machine 1 can be controlled to vary the temperature of the air, the flow rate, the duration of the applied air flow, and the phase(s) during specimen processing for drying the specimen 3. For example, after completing a staining phase, dryer 4 can direct a flow of air at approximately 120° F. at a rate of 10 liters per minute for a period of 7 seconds across the specimen. Other air temperatures (e.g., ambient temperature up to 300° F.), air flow rates (e.g., one liter per minute to 100 liters per minute), and air flow periods (e.g., from a few seconds to several minutes) can also be used.

Specimen Examination Systems

Figure 15:
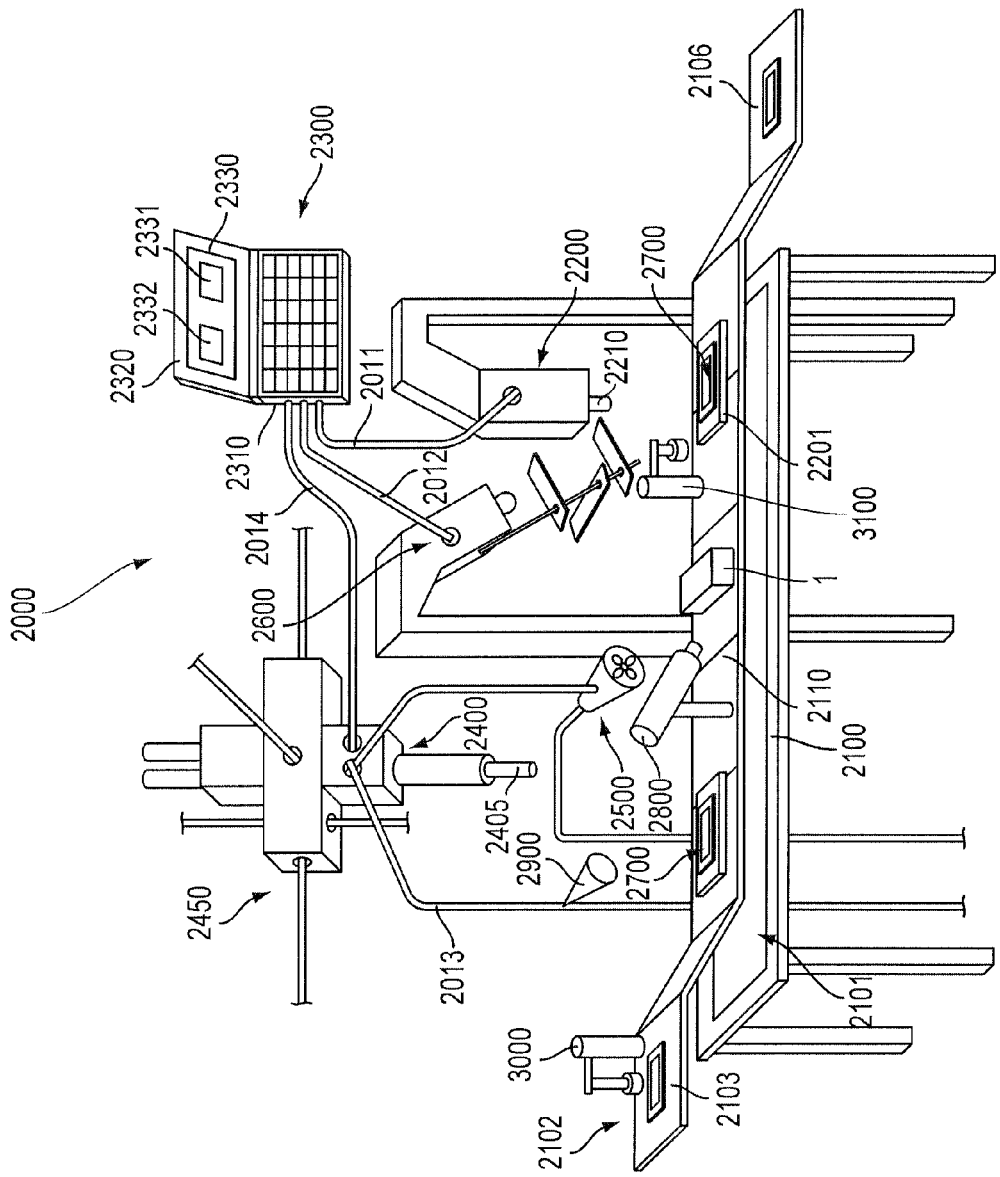
FIG. 15 is a perspective view of a specimen preparation apparatus as used in a larger specimen examination system.

The automated specimen preparation machines and apparatus disclosed herein, including machine 1, can generally be used with, and/or incorporated into, larger specimen examination systems, such as those described in U.S. Patent Application Publication No. 2009/0269799, the entire contents of which are incorporated herein by reference. For example, FIG. 15 shows a schematic diagram that illustrates one possible embodiment of a specimen examination system 2000. System 2000 includes a platform 2100, a light receiving device 2200, a computer 2300, an applicator 2400, a gas circulation device 2500, a light source 2600, a dispenser 2800, a discharge device 2900, a slide labeler 3000, and slide label reader 3100. An advancer 2110 may be configured to receive one or more slides or other substrates 2700. The advancer 2110 may be attached to a surface, such as the top surface 2101, of the platform. The advancer 2110 may take the form of a belt, and the system may use a mechanical arm, gravity, magnetism, hydraulics, gears, or other locomotion techniques to move substrate-mounted specimens along the surface 2101 of the platform.

The platform 2100 may also include a feeder 2102 and a collector 2106 for respectively feeding and collecting substrates 2700 (e.g., slides) from or to a stack or rack. Feeder 2102 may be equipped with a feeder propulsion mechanism 2103 (such as rubberized wheels) for pushing the specimens onto advancer 2110. Alternatively, a mechanical arm could be used to grab substrates 2700 and place the substrates on the advancer directly. Alternate mechanisms to propel the substrates out of feeder 2102 may be used such as magnets or hydraulics. The feeder may include a sensor for determining how many slides are present. The sensor could measure the weight of substrates 2700 for example to determine how many substrates are present. Collector 2106 can also include a sensor for determining how many substrates are present. The sensor can be configured to inform the computer 2300 when a preset number of specimens have been analyzed, and/or can inform the computer of the receipt of a specimen mounted on a substrate on an ongoing basis.

Light receiving device 2200 can be a microscope (such as brightfield microscope), a video camera, a still camera, or other optical device that receives light. Embodiments that include a standard brightfield microscope can also include an automated stage (e.g., a substrate mover 2201) and an automated focus. In some embodiments, a microscope can be attached to a motorized stage and a focus motor attachment. The microscope can have a motorized nosepiece for allowing different magnification lenses to be selected under the control of computer 2300. A filter wheel can be used to enable the computer 2300 to automatically select narrow band color filters in the light path. LED illumination can be substituted for the filters, and the use of LEDs can reduce the image acquisition time as compared to the time required for filter wheel rotation. For example, a 1600×1200 pixel FireWire® (IEEE1394 High Performance Serial Bus) camera can be used to acquire the narrow band images.

In some embodiments, light receiving device 2200 receives light reflected from substrate 2700 and stores one or more images formed by the reflected light. Alternatively, or in addition, in some embodiments, fluorescent emission from the specimen on the substrate can be detected by light receiving device 2200.

In certain embodiments, light receiving device 2200 is configured to obtain transmission images of specimens on substrates. For example, light emission source 2600 can be positioned below the platform and may direct light so that it passes through platform 2100 and substrate 2700 into light receiving device 2200.

Light receiving device 2200 and any of the other components shown in FIG. 15 can be interfaced with the computer 2300 through links (2011-2014), which can provide energy to the component, provide instructions from computer 2300 to the component, and/or allow the component to send information to computer 2300. Links 2011-2014 can be wired links or wireless links.

Light receiving device 2200 may be capable of X, Y, and Z axial movement (in other embodiments, a motorized stage or substrate mover 2201 may provide X, Y, and Z movement). Light receiving device 2200 can include pan, tilt, and/or locomotive actuators to enable computer 2300 to position light receiving device 2200 in an appropriate position. Light receiving device 2200 can include a lens 2210 that focuses incoming light.

Light receiving device 2200 can be selected to capture black and white and/or color images. In some embodiments, two or more light receiving devices can be used to divide the processing time associated with capturing the images. For example, a low magnification imaging station can be followed by a high magnification imaging station. Similarly, in some embodiments, system 2000, platform 2100, computer 2300, and/or light receiving device 2200 can direct substrate mover 2201 to move substrate 2700 to ensure the capture and storage of one or more images of all, or most, of the cells on the substrate or on a specific portion of the substrate.

Computer 2300 can be a laptop, a server, a workstation, or any other type of computing device. The computer can include a processor, a display 2320, an interface 2310, and internal memory and/or a disk drive. Computer 2300 can also include software stored in the memory or on computer readable, tangible media such as an optical drive. The software may include instructions for causing the computer to operate light receiving device 2200, applicator 2400, gas circulation device 2500, platform 2100, advancer 2110, light source 2600, dispensers 2450 and/or 2800, specimen preparation machine 1, or any component within or connected to one of these components. Similarly, the computer is arranged to receive information from any of these components.

For example, the software may control the rate of dispersal of substrates from the feeder 2102, and feeder 2102 may inform the computer about the number of substrates present. In addition, computer 2300 can also be responsible for performing the analysis of the images captured by light receiving device 2200. Through the analysis process, the computer can be arranged and controlled to calculate the number of a specific type of cell in a particular volume of blood, for example for blood, red cell, white cell, and platelet counts and other measured and derived components of the complete blood count such as: hemoglobin content, red blood cell morphology, or white blood cell count differential could be calculated. The image analysis software can analyze each individual field and sum the total red and white cell counts. To calculate the total counts per microliter in a patient blood sample, the number counted on the slide can be multiplied by the dilution ratio and volume of the sub-sample. Results of the counts, morphologic measurements, and images of red blood cells and white blood cells from the slide may be shown on the display 2320.

In some embodiments, computer 2300 is configured to display numerical data, cell population histograms, scatter plots, and direct assessments of cellular morphology using images of blood cells displayed on the monitor. The ability to display cellular morphology provides users of system 2000 the ability to quickly establish the presence or absence of abnormalities in cell morphology that may warrant preparing an additional slide for manual review by an experienced technician or other professional. The software can also provide the computer with instructions to display images 2331 received from the light receiving device or may cause display 2330 to show the results 2332 (in perhaps a chart or graph, for example) of an analysis of the images. Similarly, computer 2300 can be controlled to enumerate the number of cells of a specific type in a particular blood volume or enumerate the number of damaged cells, cancerous cells, or lysed cells in a particular volume of blood. The software enables the computer to perform the analysis process. The computer can use one or more magnifications during the analysis.

Although shown as one component, computer 2300 can include multiple computers; a first computer can be used for controlling the components of system 2000, and a second computer can be used for processing the images from light receiving device 2200. The various computers can be linked together to allow the computers to share information. Computer 2300 can also be connected to a network or laboratory information system to allow the computer to send and receive information to other computers.

In certain embodiments, applicator 2400 can include a syringe, a manual or motor driven pipettor, or a motor-controlled pump attached through a tube to a pipette tip. Applicator 2400 applies a specimen to substrate 2700 in controlled fashion. Exemplary features, attributes, and methods of using applicator 2400 are disclosed, for example, in U.S. Patent Application Publication No. US 2009/0269799. The specimen can include one or more blood components, cells, tissue, or other biological components.

Once the specimen has been applied to substrate 2700, the applied specimen is processed using machine 1. Machine 1 functions as described herein to apply one or more stains, fixatives, and/or other solutions to the specimen on the substrate.

In some embodiments, system 2000 can be configured to achieve minimal overlapping between cells deposited on substrate 2700 by laying down non-touching rows of cells from the tip of applicator 2400. Increasing viscosity of the diluted fluid or the type or amount of diluent may affect the width of the final settlement positions of specimen flows from the applicator. By selecting a distance between rows to allow for the typical variation in blood samples, all cells can be counted in all samples.

Gas movement device 2500, which can be a separate device as shown in FIG. 15, or can be incorporated into machine 1 as discussed previously, can include a fan and/or may include other gas movement devices such as a compressor or a bellows for example. Gas movement device 2500 may be connected directly to the computer 2300 or may be connected through another component such as platform 2100 or applicator 2400. The gas movement device pushes gas (in some cases atmospheric air) across the substrate to control the rate at which substances on the substrate dry. Moving too much air too quickly (i.e., too high of a fan speed) across the substrate can cause cells in the specimen to burst due to rapid drying, and too little air too slowly (i.e., too low of a fan speed) across the substrate can cause the cells to dry too slowly and appear to shrink.

Computer 2300 can select and control the amount of air that moves across the substrate in a period of time (i.e., the cubic feet or cubic centimeters of air per second) based upon the distance the gas movement device is from the substrate, the type of fluid being analyzed, the width of the flows, the temperature of the gas (e.g., air), and the average thickness of the flows. Gas movement device 2500 can be positioned so that the device directs gas so that the gas strikes the substrate at an angle of 30°-60° (e.g., 45°) for a period of about 15 to 20 seconds. In some embodiments, computer 2300 can control humidity and temperature settings in the vicinity of the system to allow the drying process to occur without the use of a gas movement device 2500.

Light emission device 2600, and the various components thereof, are described by way of example in U.S. Patent Application Publication No. US 2009/0269799. Various wavelengths of light can be generated by light emission device 2600 and detected by light receiving device 2200. For example, wavelengths such as 415 nm are useful for obtaining a hemoglobin-only image for assessing RBC morphology and hemoglobin content. Light emitted at 600 nm may be useful to provide high contrast images for platelets and nuclei. Other wavelengths may be chosen in order to best discriminate the colors of basophils, monocytes, lymphocytes (all shades of blue), eosinophils (red), and neutrophils (neutral color).

EXAMPLES

The disclosure is further described by the following examples, which are not intended to limit the scope of the invention recited in the claims.

Example 1

Figure 16:
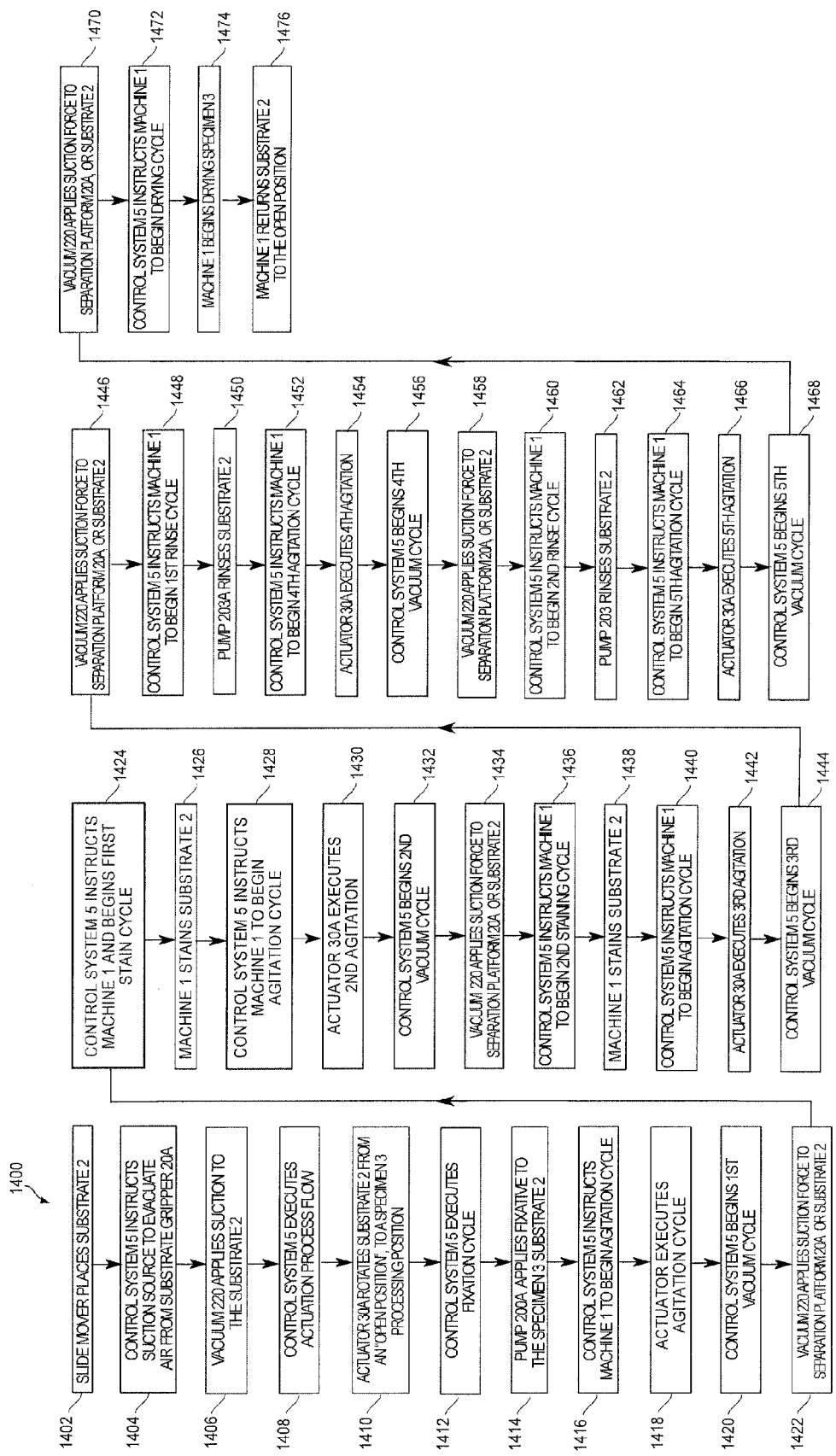
FIG. 16 is a flow chart showing a series of steps for processing a specimen mounted on a substrate.

FIG. 16 is a flow chart 1400 showing a series of exemplary steps for processing a specimen mounted on a substrate. The steps in flow chart 1400 can be used to prepare a biological specimen for examination. Although the description of this process at times refers to specific steps having specific ranges, and/or discloses steps occurring in a specific sequence, this description is intended solely as a non-limiting example. With reference to FIG. 16, machine 1 is connected to a control system 5 for commanding the operation of various machine components during the processing steps. In a specimen initiation step, a biological specimen 3 that includes red blood cells, white blood cells, and platelets from an aliquot of blood is applied to a substrate 2 consisting of a glass microscope slide. This can be performed using a different station such as one or more of the stations described in co-pending U.S. Patent Application Publication No. 2008/0102006. In a positioning step 1402, substrate 2 containing specimen 3 is loaded onto substrate gripper 20A of substrate arm 10A as shown in FIG. 1. Control system 5 instructs suction source 222 (step 1404) to evacuate air from the substrate gripper 20A. Suction applied through suction ports 21 and 22 (step 1406) adheres the substrate 2 to the substrate gripper 20A during specimen processing. Control system 5 instructs (step 1408) the actuator 30A to rotate the substrate 3 from an open position shown in FIG. 1 to a specimen processing position shown in FIG. 3A. In the specimen processing position, specimen 3 faces the surface of platform 60A while substrate 2 rests against offsets 70A-D shown in FIG. 2. The offsets prevent the substrate 2 from making contact with the surface of platform 60A. In this example process, the separation 92 between the specimen-containing surface of substrate 2 and the surface of platform 60A is approximately 100 microns.

During the fixation phase (step 1412, see also FIG. 10), a pump applies fixative to the specimen 3 in step 1414. Pump 200A connected to fluid tube 54A shown in FIG. 2 propels fixative comprising methanol from a fixative reservoir 210 through tube 54A, out port 44A, onto platform 60A, onto substrate 2 containing specimen 3, and into the separation 92 between platform 60A and substrate 2. Pump 200A propels methanol from port 44A at a flow rate of 70 microliters per second for a two second period T1, thereby directing a total of 140 microliters of methanol, V1, onto substrate 2 containing specimen 3.

Figure 17:
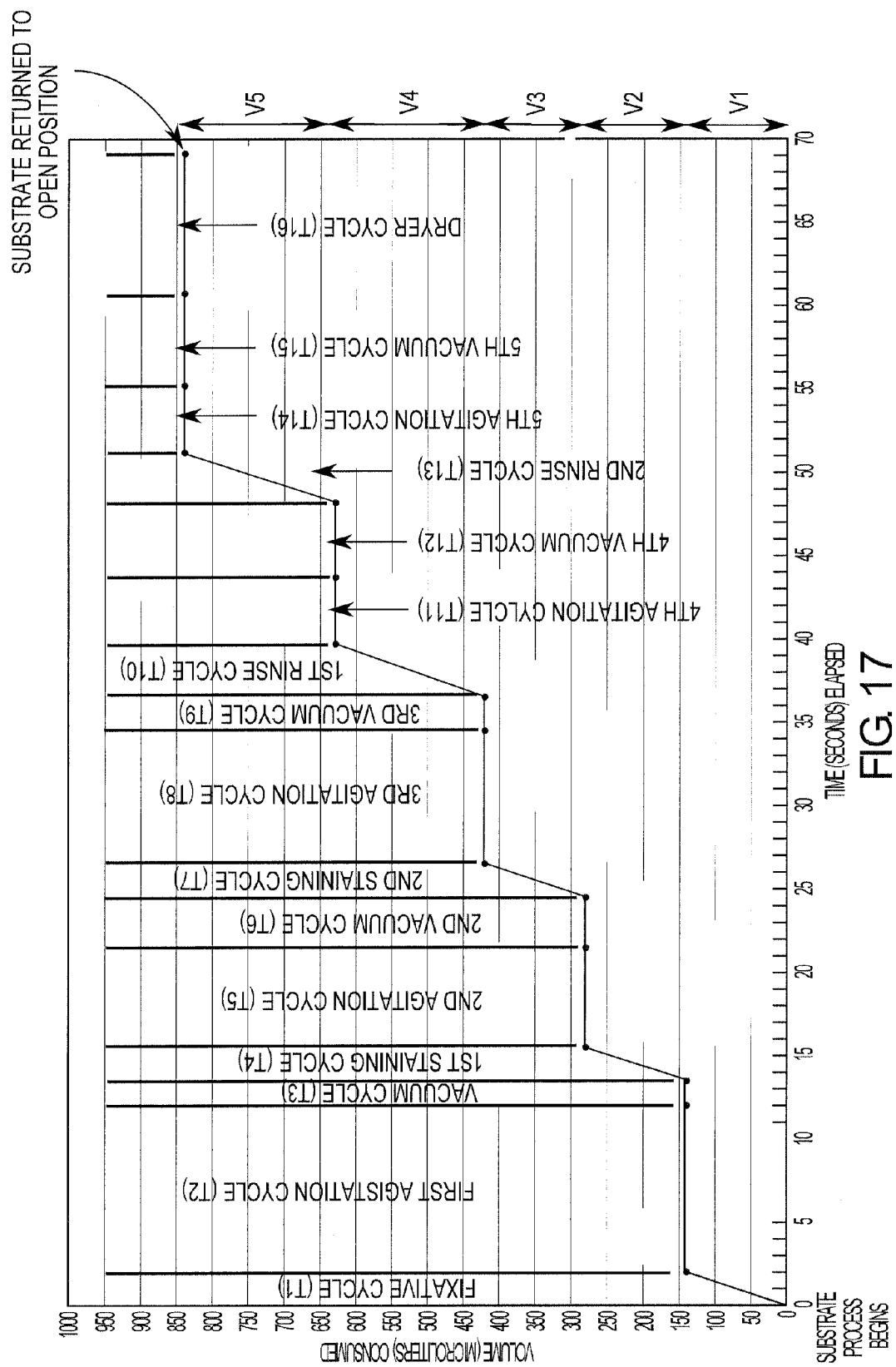
FIG. 17 is a graph showing volume of fluid consumed as a function of time in the flow chart of FIG. 16.

Next, in a first agitation step 1416, control system 5 agitates the substrate by directing actuator 30A (step 1418) to raise the proximate edge of substrate 2 vertically a distance of 35 microns from the specimen processing position and returning the substrate to its specimen processing position. Machine 1 repeats this agitation step four more times. The machine 1 completes the five agitation movements in approximately ten seconds, T2, as shown in FIG. 17. After agitation, the control system initiates a vacuum or evacuation step 1420. A vacuum force of negative five psi is applied for one and a half seconds, T3, evacuating any residual methanol (step 1422) present in the separation, on the platform, or on the substrate via ports 40A and 41A, and waste tubes 50A and 51A. The evacuated methanol is collected in a waste container 230 and/or 231.

Following the fixing phase, control system 5 initiates (step 1424) a first staining phase. In doing so, control system 5 directs the machine 1 to stain the specimen (step 1426). Referring to FIG. 2 and the flowchart of FIG. 11, pump 201 connected to fluid tube 52A propels fluorescein dye from a stain reservoir 211A out port 42A, onto platform 60A, onto substrate 2 containing specimen 3, and into the separation 92 between the platform 60A and substrate 2. Pump 201 dispenses fluorescein dye through port 42A at a flow rate of 70 microliters per second for a two second period, T4, thereby directing 140 microliters of dye, V2, onto the substrate.

After applying fluorescein dye to specimen 3, machine 1 performs a second agitation step 1428 by directing actuator 30A to raise, in step 1430, the proximate edge of substrate 2 vertically a distance of 35 microns from the specimen processing position and then return the substrate to its specimen processing position. Control system 5 causes the machine 1 to repeat this agitation step two more times and complete the three agitations over a period of approximately six seconds, T5, as shown in FIG. 17.

Next a second vacuum or evacuation phase is initiated in step 1432. A vacuum of negative five psi applied for three seconds, T6, in step 1434 to evacuate any residual fluorescein dye present in the separation 92 or on the platform and substrate via ports 40A and/or 41A, and waste tubes 50A and 51A. The evacuated fluorescein dye is collected in a waste container 230A and/or 231 A.

After staining the specimen with fluorescein dye, machine 1 initiates a second staining phase in step 1436 using thiazin dye. Pump 202 connected to fluid tube 53A propels thiazin dye from a stain reservoir through port 43A, onto platform 60A, onto substrate 2, and into the separation 92 between platform 60A and substrate 2 (step 1438). Machine 1 dispenses thiazin dye through port 43A at a flow rate of 70 microliters per second for a two second period, T7, thereby directing a total of 140 microliters of thiazin dye, V3, onto the substrate.

After applying stain to specimen 3, machine 1 initiates a third agitation phase in step 1440 by directing actuator 30A to raise the proximate edge of substrate 2 (step 1442) a distance of 35 microns from the specimen processing position and then return the substrate containing specimen 3 to its specimen processing position. Machine 1 repeats this agitation step three more times. The machine completes the four agitation movements over a period of approximately eight seconds, T8.

A third vacuum or evacuation step 1444 is then initiated. A vacuum of negative five psi is applied for two seconds, T9, to evacuate residual thiazin dye in step 1446 present in the separation or on the platform 60A and substrate 2 via ports 40A and/or 41A, and waste tubes 50A and/or 51A, after agitation. The evacuated thiazin dye is collected in a waste container 230A and/or 231A.

Machine 1 then performs two rinse-agitation-vacuum phase sequences. The first sequence of phases is initiated at step 1448 when control system 5 instructs machine 1 to initiate a first rinse phase. A reservoir 213A containing rinse solution of distilled water is connected to a pump 203 and fluid tube 55A. Pump 203 directs distilled water through wash tube 55A that feeds into port 45A, into the separation 92, and onto platform 60A and substrate 2 to rinse specimen 3 in step 1450. Alternatively, in some embodiments, wash fluid is directed through two or more of fluid ports 42A to 45A. Pump 203 directs distilled water out of ports 45A at a flow rate of 70 microliters per second for two seconds, T10, thereby directing a total of 140 microliters, V4, of water onto the substrate containing the specimen.

Next, control system 5 initiates a fourth agitation phase in step 1452, directing actuator 30A (step 1454) to raise the proximate edge of substrate 2 vertically a distance of 35 microns from the specimen processing position and returning the substrate to its specimen processing position. Control system 5 may direct the machine 1 to repeat this agitation phase, and complete the two agitations in approximately four seconds, T11.

Then, a vacuum or evacuation phase is initiated in step 1456. A vacuum of five psi applied for five and a half seconds, T12, in step 1458, evacuates residual distilled water present in the separation 92 or on the platform 60A and substrate 2 via ports 40A and/or 41A, and waste tubes 50A and/or 51A after agitation.

Thereafter, in step 1460, control system 5 directs machine 1 to begin the second rinse-agitation-vacuum phase sequence by initiating a second rinse phase. A second rinse phase (steps 1460, 1462), a fifth agitation phase (steps 1464, 1466), and a fifth vacuum phase (steps 1468, 1470) are performed in the same manner as disclosed above for the first rinse-agitation-vacuum phase. During the second rinse-agitation-vacuum phase, the amount of wash fluid, V5, and the processing times T13, T14, and T15 are generally the same as in the first rinse-agitation-vacuum phase sequence.

After the specimen has been fixed, stained with fluorescein and thiazin stains, and rinsed, machine 1 initiates a drying phase in step 1472. Dryer 4 directs an air flow of approximately 120° at a 10 liter-per-minute flow rate (step 1474) for an eight second period, T16, across the specimen.

Following completion of these steps, substrate 2 is returned to its original position in step 1476. In this step, actuator 30A rotates substrate 2 from the specimen processing position to the open position as depicted in FIG. 1. Substrate 2 may then be removed by a substrate mover, and a new substrate may be loaded for processing a new specimen.

Example 2

The processing steps described above for Example 1 may be adjusted in other embodiments of the invention as follows.

In addition, fixative, stains, and rinse solution formulations disclosed in U.S. Provisional Patent Application No. 61/505,011 can be used in the following example processing steps.

During a first fixation phase (step 1412, see also FIG. 10), a pump applies a fixative solution to the specimen 3 in step 1414. Pump 200A connected to fluid tube 54A shown in FIG. 2 propels a fixative solution comprising methanol from a fixative reservoir 210 through tube 54A, out port 44A, onto platform 60A, onto substrate 2, and into the separation 92 between platform 60A and substrate 2. Pump 200A propels the fixative solution from port 44A at a flow rate of 115 microliters per second for a two second period T1, thereby directing a total of 230 microliters of the fixative solution, V1, onto substrate 2.

Next, in a first agitation step 1416, control system 5 agitates the substrate by directing actuator 30A (step 1418) to raise the proximate edge of substrate 2 vertically a distance of 35 microns from the specimen processing position and returning the specimen to its specimen processing position. Machine 1 repeats this agitation step five more times. The machine 1 completes the six agitation movements in approximately 12 seconds. After agitation, the control system initiates a vacuum step 1420. A vacuum force of negative six psi is applied for one and a half seconds, T3, evacuating any residual fixative solution (step 1422) present in the separation, on the platform, or on the substrate via ports 40A and 41A, and waste tubes 50A and 51A. The evacuated fixative solution is collected in a waste container 230 and/or 231.

Thereafter, in a second fixation phase including a second agitation step, the foregoing steps of the first fixation phase and first agitation step are repeated.

Following the fixing phases, control system 5 initiates (step 1424) a first staining phase. In doing so, control system 5 directs the machine 1 to stain the specimen (step 1426). Referring to FIG. 2 and the flowchart of FIG. 11, pump 201 connected to fluid tube 52A propels a first stain solution comprising eosin Y from a stain reservoir 211A out port 42A, onto platform 60A, onto substrate 2 including specimen 3, and into the separation 92 between the platform 60A and substrate 2. Pump 201 dispenses the first stain solution through port 42A at a flow rate of 115 microliters per second for a two second period, T4, thereby directing 230 microliters of the first stain solution, V2, onto the substrate.

After applying a first stain solution to specimen 3, machine 1 performs a second agitation step 1428 by directing actuator 30A to raise, in step 1430, the proximate edge of substrate 2 vertically a distance of 35 microns from the specimen processing position and then return the specimen to its specimen processing position. Control system 5 causes the machine 1 to repeat this agitation step two more times and complete the three agitations over a period of approximately six seconds, T5, as shown in FIG. 17.

Next a second vacuum phase is initiated in step 1432. A vacuum of negative five psi applied for three seconds, T6, in step 1434 to evacuate any residual first stain solution present in the separation 92 or on the platform and substrate via ports 40A and/or 41A, and waste tubes 50A and 51A. The evacuated first stain solution is collected in a waste container 230A and/or 231 A.

After staining the specimen with the first stain solution including eosin Y, machine 1 initiates a second staining phase in step 1436 using a second stain solution including azure B and methylene blue. Pump 202 connected to fluid tube 53A propels the second stain solution from a stain reservoir through port 43A, onto platform 60A, onto substrate 2, and into the separation 92 between platform 60A and substrate 2 (step 1438). Machine 1 dispenses the second stain solution through port 43A at a flow rate of 115 microliters per second for a two second period, T7, thereby directing a total of 230 microliters of the second stain solution, V3, onto the substrate.

After applying stain to specimen 3, machine 1 initiates a third agitation phase in step 1440 by directing actuator 30A to raise the proximate edge of substrate 2 (step 1442) a distance of 35 microns from the specimen processing position and then return the specimen 3 to its specimen processing position. Machine 1 repeats this agitation step two more times. The machine completes the three agitation movements over a period of approximately six seconds, T8.

A third vacuum step 1444 is then initiated. A vacuum of negative six psi is applied for two seconds, T9, to evacuate residual second stain solution in step 1446 present in the separation or on the platform 60A and substrate 2 via ports 40A and/or 41A, and waste tubes 50A and/or 51A, after agitation. The evacuated second stain solution is collected in a waste container 230A and/or 231A.

Machine 1 then performs two rinse-agitation-vacuum phase sequences. The first sequence of phases is initiated at step 1448 when control system 5 instructs machine 1 to initiate a first rinse phase. A reservoir 213A containing a rinse solution is connected to a pump 203 and fluid tube 55A. Pump 203 directs the rinse solution through wash tube 55A that feeds into port 45A, into the separation 92, and onto platform 60A and substrate 2 to rinse specimen 3 in step 1450. Alternatively, in some embodiments, rinse solution is directed through two or more of fluid ports 42A to 45A. Pump 203 directs the rinse solution out of ports 45A at a flow rate of 115 microliters per second for two seconds, T10, thereby directing a total of 230 microliters, V4, of water onto the substrate.

Next, control system 5 initiates a fourth agitation phase in step 1452, directing actuator 30A (step 1454) to raise the proximate edge of substrate 2 vertically a distance of 35 microns from the specimen processing position and returning the specimen to its specimen processing position. Control system 5 then directs the machine 1 to repeat this agitation phase three more times, and complete the four agitations in approximately eight seconds, T11.

Then, a vacuum phase is initiated in step 1456. A vacuum of five psi applied for five and a half seconds, T12, in step 1458, evacuates residual rinse solution present in the separation 92 or on the platform 60A and substrate 2 via ports 40A and/or 41A, and waste tubes 50A and/or 51A after agitation.

Thereafter, in step 1460, control system 5 directs machine 1 to begin the second rinse-agitation-vacuum phase sequence by initiating a second rinse phase. A second rinse phase (steps 1460, 1462), a fifth agitation phase comprising six agitations completed in approximately 12 seconds, and a fifth vacuum phase (steps 1468, 1470) are performed in the same manner as disclosed above for the first rinse-agitation-vacuum phase. During the second rinse-agitation-vacuum phase, the amount of rinse solution, V5, and the processing times T13, T14, and T15 are generally the same as in the first rinse-agitation-vacuum phase sequence. In addition, immediately prior to the vacuum phase, actuator 30A raises the proximate edge of substrate 2 a distance of 15-35 microns from the specimen processing position. This increased separation between substrate 2 and platform 60 improves evacuation of any residual fluids in separation 92 during the final vacuum phase.

After the specimen has been fixed, stained with a first stain solution containing eosin Y and a second staining solution containing azure B and methylene blue, and rinsed, machine 1 initiates a drying phase in step 1472. Dryer 4 directs an air flow of approximately 120° at a 10 liter-per-minute flow rate (step 1474) for an eight second period, T16, across the specimen.

Following completion of these steps, substrate 2 is returned to its original position in step 1476. In this step, actuator 30A rotates substrate 2 from the specimen processing position to the open position as depicted in FIG. 7. Substrate 2 may then be removed by a substrate mover, and a new substrate may be loaded for processing a new specimen.

As illustrated in the example specimen processing steps described above, the systems and methods disclosed herein provide for more efficient specimen processing by consuming fewer reagents as compared to conventional specimen processing methods including automated and manual specimen preparation techniques. Referring to Example 2, machine 1 consumed less than one and a half milliliters of reagents for fixing, staining, and rinsing the specimen during the exemplary processing steps (e.g., 460 microliters of fixative solution+230 microliters of first stain solution+230 microliters of second stain solution+460 microliters of rinse solution=1380 microliters of reagents). In some embodiments, more or less than 1380 microliters of fluids can be used during specimen processing. For example, the amount of fluid used in processing a specimen can be approximately 1150 microliters (e.g., by eliminating one of the rinse phases) or less than 1,000 microliters (e.g., by further eliminating one of the fixative phases).

With respect to FIG. 17, for Example 1, machine 1 consumed less than one milliliter of reagents for fixing, staining, and rinsing the specimen during the exemplary processing steps (e.g., 140 microliters of methanol fixative+140 microliters of fluorescein dye+140 microliters of thiazin dye+280 microliters of rinse solution=700 microliters of reagents). In some embodiments, more or less than 700 microliters of fluids can be used during specimen processing. For example, the amount of fluid used in processing a specimen can be approximately 560 microliters (e.g., by eliminating one of the rinse phases).

In general, the total volume of fluids consumed can be 500 microliters or more (e.g., 520 microliters or more, 540 microliters or more, 560 microliters or more, 580 microliters or more, 600 microliters or more, 650 microliters or more, 700 microliters or more, 750 microliters or more) and/or 2 mL or less (e.g., 1.5 mL or less, 1.4 mL or less, 1.3 mL or less, 1.2 mL or less, 1.1 mL or less, 1.0 mL or less, 900 microliters or less).

Referring to FIG. 17 and Example 1, the specimen preparation process is completed in slightly more than one minute (e.g., 13.5 seconds elapsed during the fixing phase+11 seconds elapsed during the fluorescein dye phase+12 seconds elapsed during the thiazin dye phase+23 seconds elapsed during the rinse phases+8 seconds elapsed during the drying phase=67.5 seconds total elapsed time). In certain embodiments, specimen preparation can be completed in more, as in Example 2, or less than 67.5 seconds. For example, specimen processing can be completed in 180 seconds or less (e.g., 150 seconds or less, 120 seconds or less, 90 seconds or less, 80 seconds or less, 70 seconds or less, 60 seconds or less, 50 seconds or less, or 40 seconds or less).

Further, while the foregoing exemplary process describes processing time for a single specimen, systems and methods for processing multiple substrates (e.g., machine 1 in FIG. 1, configured to process two substrates, and/or systems configured to process three or more substrates) are capable of processing more than 100 specimens per hour (e.g., between 60 specimens and 120 specimens per hour). Use of the systems and methods disclosed herein in laboratory settings can result in faster throughput on a per specimen basis, while consumption of fluids (e.g., fixative, stain, and rinse fluids) is reduced compared to conventional automated systems and manual specimen preparation techniques.

Other Embodiments

It is to be understood that while the invention has been described in conjunction with the detailed description, the foregoing description is intended to illustrate and not limit the scope of the disclosure, which is defined by the scope of the appended claims. Other aspects, advantages, and modifications are within the scope of the following claims.

What is claimed is:

1. An apparatus for preparing a biological specimen on a substrate for examination, the apparatus comprising:
    a substrate arm including a substrate gripper;
    a first actuator connected to the substrate arm and configured to move the substrate arm between an open position and a specimen processing position;
    a second actuator arranged and configured to agitate a substrate gripped by the substrate gripper on the substrate arm;
    a platform having a top surface located opposite the substrate when the substrate arm is in the specimen processing position; and
    two or more offsets arranged on the top surface of the platform such that when the substrate contacts all of the offsets in the substrate processing position, the substrate and top surface of the platform are substantially parallel and form a separation of at least about 50 microns.

2. The apparatus of claim 1, wherein the first and second actuator are the same actuator configured to both move the substrate arm and to agitate a substrate gripped by the substrate gripper on the substrate arm.

3. The apparatus of claim 1, wherein a total surface area of the top surface of the platform is smaller than a total surface area of the substrate.

4. The apparatus of claim 3, further comprising a support block having a recess, wherein:
    the platform is positioned within the recess of the support block; and
    the top surface of the substrate is elevated relative to a top surface of the support block, so that fluid from the top surface of the substrate can be collected within the recess.

5. The apparatus of claim 1, wherein there are at least three offsets arranged at outer edges of the top surface of the platform and wherein tips of the offsets define a plane.

6. The apparatus of claim 1, further comprising a suction port located on the substrate gripper; the suction port connectable to a suction source for providing suction to the suction port through a suction tube, to thereby hold the substrate to the substrate gripper.

7. The apparatus of claim 1, further comprising a first stain port located on the top surface of the platform, a first stain reservoir, and a first stain conduit connected to the first stain port for providing a fluid pathway for stain to be pumped from the first stain reservoir to the first stain port and into the separation.

8. The apparatus of claim 7, further comprising a second stain port located on the top surface of the platform at a location different from the first stain port location, a second stain reservoir, and a second stain conduit, wherein both the first and second stain ports are arranged on the top surface at a spacing from a specimen area on the substrate when the substrate is in the specimen processing position, and wherein the second stain conduit is connected to the second stain port to provide a fluid pathway for stain to be pumped from the second stain reservoir to the second stain port and into the separation.

9. The apparatus of claim 7, further comprising a first fixative port located on the top surface of the platform, a fixative reservoir, and a fixative conduit connected to the first fixative port for providing a fluid pathway for fixative to be pumped from the fixative reservoir to the first fixative port and into the separation.

10. The apparatus of claim 9, further comprising a first rinse port located on the top surface of the platform, a rinse solution reservoir, and a rinse tube connected to the first rinse port for providing a fluid pathway for rinse fluid to be pumped from the rinse solution reservoir to the first rinse port and into the separation.

11. The apparatus of claim 1, further comprising a first vacuum port located on the top surface of the platform, a first waste container, and a first waste conduit connected to the first vacuum port for providing a pathway of negative pressure to evacuate fluid from the separation or substrate and deposit the fluid into the first waste container.

12. The apparatus of claim 11, further comprising a second vacuum port located on the top surface of the platform and a second waste conduit connected to the second vacuum port for providing a pathway of negative pressure to evacuate fluid from the separation or substrate and deposit the fluid into the first waste container.

13. The apparatus of claim 12, wherein the first and second vacuum ports are located on opposite ends of the top surface of the platform.

14. The apparatus of claim 1, wherein the platform further comprises:
a fixative port;
a first stain port;
a second stain port;
a rinse port;
a first vacuum port; and
a second vacuum port.

15. The apparatus of claim 14, further comprising a block arranged to support the platform, wherein the block comprises:
a fixative port;
a first stain port;
a second stain port;
a rinse port;
a first vacuum port; and
a second vacuum port;
wherein each port on the block is in a location corresponding to a port located in the platform.

16. The apparatus of claim 1, further comprising:
a first stain reservoir;
a second stain reservoir;
a fixative reservoir;
a rinse solution reservoir;
a waste container;
a pump;
a plurality of fluid conduits connected to the pump and to the reservoirs and arranged for dispensing fluid from any one or more of the reservoirs; and
a vacuum source for evacuating fluid from the substrate into the waste container.

17. The apparatus of claim 1, further comprising a dryer positioned to direct a flow of air across the specimen when the substrate is located in the open position.

18. An automated specimen examination system comprising:

an applicator station that applies a sample specimen to a substrate;
the biological specimen preparation apparatus of claim 1; and
an imaging station that images the biological specimen after preparation by the specimen preparation apparatus.

19. The apparatus of claim 1, further comprising an alignment mechanism configured to position the substrate gripper relative to the substrate arm, the alignment mechanism comprising:
a first member connected to the substrate arm and comprising an opening and a clamping member; and
a second member connected to the substrate gripper and configured to be positioned within the opening,
wherein when the second member is positioned within the opening, a first side of the second member is positioned to contact a surface of the first member, and the clamping member is positioned to apply a force to a second side of the second member opposite to the first side.

20. The apparatus of claim 19, wherein the alignment mechanism further comprises a deflection element positioned between the second member and the substrate gripper, and wherein:
at least a portion of an outer surface of the second member has a spherical shape; and
the second member comprises an internal aperture configured to receive a fastener that rigidly connects the second member to the substrate gripper.

21. The apparatus of claim 1, wherein the substrate arm is a first substrate arm and the substrate gripper is a first substrate gripper, and further comprising:
a second substrate arm including a second substrate gripper; and
a translation apparatus configured to translate the apparatus between at least two positions, wherein in a first one of the positions, the first substrate gripper is positioned to retrieve a substrate from a substrate mover, and in a second one of the positions, the second substrate gripper is positioned to retrieve a substrate from the substrate mover.

22. The apparatus of claim 21, further comprising a control system connected to the translation mechanism, wherein the control system is configured so that during operation of the apparatus, the control system activates the translation mechanism so that:
when a substrate is attached to the second substrate gripper and the second substrate arm is at the open position, at the specimen processing position, or at a position intermediate between the open position and the specimen processing position, the first substrate gripper is positioned to retrieve a substrate from the substrate mover; and
when a substrate is attached to the first substrate gripper and the first substrate arm is at the open position, at the specimen processing position, or at a position intermediate between the open position and the specimen processing position, the second substrate gripper is positioned to retrieve a substrate from the substrate mover.

23. The apparatus of claim 1, further comprising:
first and second vacuum ports located on opposite sides of the top surface of the platform;
at least one waste container; and
waste conduits connected to the first and second vacuum ports for providing a pathway of negative pressure to evacuate fluid from the separation or substrate and deposit the fluid into the at least one waste container.

24. The apparatus of claim 1, further comprising a control system connected to the first and second actuators, wherein the control system is configured so that during operation of the apparatus, the control system activates the first actuator to displace the substrate from the specimen processing position before fluid is removed from the separation.

25. The apparatus of claim 1, further comprising a control system connected to a fixative dispersal subsystem comprising a fixative port located on the top surface of the platform, a fixative reservoir, and a fixative conduit, wherein the control system is configured to prepare a biological specimen on a substrate by:
dispersing a fixative solution onto the substrate using the fixative dispersal subsystem; and
activating the first actuator to agitate the substrate.

26. The apparatus of claim 25, wherein the control system is connected to a vacuum subsystem comprising a vacuum port located on the top surface of the platform, a waste container, and a waste conduit connected to the vacuum port for providing a pathway of negative pressure to evacuate fluid from the separation or substrate and deposit the fluid into the waste container, and wherein the control system is further configured to prepare the biological specimen on the substrate by evacuating the fixative solution from the substrate using the vacuum subsystem.

27. The apparatus of claim 26, wherein the control system is connected to a first stain subsystem comprising a first stain port located on the top surface of the platform, a first stain reservoir, and a first stain conduit connected to the first stain port for providing a fluid pathway for stain to be pumped from the first stain reservoir to the first stain port and into the separation, and wherein the control system is further configured to prepare the biological specimen on the substrate by:
dispersing a first stain solution onto the substrate using the first stain subsystem;
activating the first actuator to agitate the substrate; and
evacuating the first stain solution from the substrate using the vacuum subsystem.

28. The apparatus of claim 27, wherein the control system is connected to a second stain subsystem comprising a second stain port located on the top surface of the platform, a second stain reservoir, and a second stain conduit connected to the second stain port for providing a fluid pathway for stain to be pumped from the second stain reservoir to the second stain port and into the separation, and wherein the control system is further configured to prepare the biological specimen on the substrate by:
dispersing a second stain solution onto the substrate using the second stain subsystem;
activating the first actuator to agitate the substrate; and
evacuating the second stain solution from the substrate using the vacuum subsystem.

29. The apparatus of claim 28, wherein the control system is connected to a rinse subsystem comprising a rinse port located on the top surface of the platform, a rinse solution reservoir, and a rinse tube connected to the rinse port for providing a fluid pathway for rinse fluid to be pumped from the rinse solution reservoir to the rinse port and into the separation, and wherein the control system is further configured to prepare the biological specimen on the substrate by:
dispersing a rinse solution onto the substrate using the rinse subsystem;
activating the first actuator to agitate the substrate; and
evacuating the rinse solution from the substrate using the vacuum subsystem.

30. The apparatus of claim 29, wherein the control system is further configured to prepare the biological specimen on the substrate by repeating the steps of dispersing a rinse solution onto the substrate using the rinse subsystem, activating the first actuator to agitate the substrate, and evacuating the rinse solution from the substrate using the vacuum subsystem, to rinse the substrate a second time.

31. The apparatus of claim 30, wherein the control system is connected to a dryer, and wherein the control system is further configured to prepare the biological specimen on the substrate by using the dryer to direct a flow of air over the substrate.

* * * * *